United States Patent
Sharei et al.

(10) Patent No.: US 11,613,759 B2
(45) Date of Patent: Mar. 28, 2023

(54) INTRACELLULAR DELIVERY OF BIOMOLECULES TO CELLS COMPRISING A CELL WALL

(71) Applicant: SQZ Biotechnologies Company, Watertown, MA (US)

(72) Inventors: Armon R. Sharei, Somerville, MA (US); Howard Bernstein, Cambridge, MA (US); Jonathan B. Gilbert, Somerville, MA (US)

(73) Assignee: SQZ Biotechnologies Company, Watertown, MA (US)

( * ) Notice: Subject to any disclaimer, the term of this patent is extended or adjusted under 35 U.S.C. 154(b) by 238 days.

(21) Appl. No.: 15/757,316

(22) PCT Filed: Sep. 2, 2016

(86) PCT No.: PCT/US2016/050288
§ 371 (c)(1),
(2) Date: Mar. 2, 2018

(87) PCT Pub. No.: WO2017/041051
PCT Pub. Date: Mar. 9, 2017

(65) Prior Publication Data
US 2018/0245089 A1    Aug. 30, 2018

Related U.S. Application Data

(60) Provisional application No. 62/365,177, filed on Jul. 21, 2016, provisional application No. 62/214,821, filed on Sep. 4, 2015.

(51) Int. Cl.
| | | |
|---|---|---|
| *C12N 15/81* | (2006.01) | |
| *C12M 1/42* | (2006.01) | |
| *C12N 15/87* | (2006.01) | |
| *C12N 15/82* | (2006.01) | |
| *G01N 1/30* | (2006.01) | |
| *B82Y 5/00* | (2011.01) | |

(52) U.S. Cl.
CPC ............. *C12N 15/81* (2013.01); *C12M 35/04* (2013.01); *C12N 15/8206* (2013.01); *C12N 15/8207* (2013.01); *C12N 15/87* (2013.01); *G01N 1/30* (2013.01); *B82Y 5/00* (2013.01)

(58) Field of Classification Search
None
See application file for complete search history.

(56) References Cited

U.S. PATENT DOCUMENTS

| | | |
|---|---|---|
| 4,055,799 A | 10/1977 | Coster |
| 4,321,259 A | 3/1982 | Nicolau |
| 4,327,710 A | 5/1982 | Deloach |
| 4,376,634 A | 3/1983 | Prior et al. |
| 4,478,824 A | 10/1984 | Franco |
| 4,652,449 A | 3/1987 | Ropars |
| 4,752,586 A | 6/1988 | Ropars |
| 4,835,457 A | 5/1989 | Hanss |
| 4,965,857 A | 10/1990 | Auracher |
| 5,023,054 A | 6/1991 | Sato |
| 5,372,942 A | 12/1994 | Mcgarrity |
| 5,589,389 A | 12/1996 | Pages |
| 5,612,207 A | 3/1997 | Nicolau |
| 5,622,963 A | 4/1997 | Armstrong |
| 5,643,577 A | 7/1997 | Pang |
| 5,736,507 A | 4/1998 | Boots |
| 5,916,793 A | 6/1999 | Filpula |
| 5,951,976 A | 9/1999 | Segal |
| 6,133,503 A | 10/2000 | Scheffler |
| 6,139,836 A | 10/2000 | Magnani |
| 6,218,166 B1 | 4/2001 | Ravindranath |
| 6,410,329 B1 | 6/2002 | Hansen |
| 6,461,867 B1 | 10/2002 | Cai |
| 6,610,702 B2 | 8/2003 | Lehn |
| 6,737,259 B1 | 5/2004 | Clark |
| 6,812,204 B1 | 11/2004 | Mchale |
| 7,037,500 B1 | 5/2006 | Silverstein |
| 7,071,297 B2 | 7/2006 | Wraith |
| 7,485,314 B2 | 2/2009 | Kakkis |
| 7,704,743 B2 | 4/2010 | Fedorov |
| 8,147,867 B2 | 4/2012 | Hong |
| 8,211,656 B2 | 7/2012 | Hyde |
| 8,679,751 B2 | 3/2014 | Huang |

(Continued)

FOREIGN PATENT DOCUMENTS

| | | |
|---|---|---|
| CN | 101031339 A | 9/2007 |
| CN | 101031641 A | 9/2007 |

(Continued)

OTHER PUBLICATIONS

Delorme, Evelyne (Transformation of *Saccharomyces cerevisiae* by Electroporation. Sep. 1989. Applied and Environmental Microbiology. pp. 2242-2246. (Year: 1989).*

Gietz et al. Genetic Transformation of Yeast. Apr. 2001. BioTechniques. vol. 20, pp. 816-831. (Year: 2001).*

Noblitt et al. Integrated Membrane Filters for Minimizing Hydrodynamic Flowing and Filtering in Microfluidic Devices. Aug. 15, 2007. Analytical Chemistry. vol. 79, No. 16, pp. 6249-6254. (Year: 2007).*

(Continued)

*Primary Examiner* — Nancy J Leith

(74) *Attorney, Agent, or Firm* — Sterne, Kessler, Goldstein & Fox P.L.L.C.

(57) ABSTRACT

The present disclosure pertains to methods for delivering a compound into a cell comprising a cell wall, including passing a cell suspension through a constriction, wherein said constriction deforms the cell comprising a cell wall, thereby causing a perturbation of the cell such that the compound enters the cell, wherein said cell suspension is contacted with the compound.

25 Claims, 3 Drawing Sheets

(56) References Cited

U.S. PATENT DOCUMENTS

| | | |
|---|---|---|
| 8,697,359 B1 | 4/2014 | Zhang |
| 8,844,570 B2 | 9/2014 | Glick |
| 9,005,579 B2 | 4/2015 | Nowinski |
| 9,255,245 B2 | 2/2016 | Bernick |
| 9,364,504 B2 | 6/2016 | Godfrin |
| 9,458,489 B2 | 10/2016 | Lim |
| 9,950,049 B2 | 4/2018 | Godfrin |
| 10,124,336 B2 | 11/2018 | Sharei |
| 10,526,573 B2 | 1/2020 | Ding |
| 10,696,944 B2 | 6/2020 | Sharei |
| 10,870,112 B2 | 12/2020 | Sharei |
| 2003/0045467 A1 | 3/2003 | Orban |
| 2003/0133922 A1 | 7/2003 | Kasha |
| 2004/0176282 A1 | 9/2004 | Dalby |
| 2004/0197898 A1 | 10/2004 | Nakatani |
| 2006/0002915 A1 | 1/2006 | Min |
| 2006/0134067 A1 | 6/2006 | Liu |
| 2006/0134772 A1 | 6/2006 | Miles |
| 2006/0188490 A1 | 8/2006 | Hoerr |
| 2006/0193869 A1 | 8/2006 | Barrat |
| 2007/0243523 A1 | 10/2007 | Ionescu-zanetti |
| 2007/0249038 A1 | 10/2007 | Adamo |
| 2008/0026465 A1 | 1/2008 | Nakata |
| 2008/0241844 A1 | 10/2008 | Kellogg |
| 2008/0261262 A1 | 10/2008 | Godfrin |
| 2008/0274092 A1 | 11/2008 | Godfrin |
| 2008/0311140 A1 | 12/2008 | Lee |
| 2008/0318324 A1 | 12/2008 | Chiu |
| 2009/0092637 A1 | 4/2009 | Ludvigsson |
| 2009/0238818 A1 | 9/2009 | Kakkis |
| 2009/0280518 A1 | 11/2009 | Adamo |
| 2010/0203068 A1 | 8/2010 | Betz |
| 2010/0249621 A1 | 9/2010 | Ichitani |
| 2010/0266571 A1 | 10/2010 | Lockhart |
| 2010/0323388 A1 | 12/2010 | Chiu |
| 2011/0014616 A1 | 1/2011 | Holmes |
| 2011/0030808 A1 | 2/2011 | Chiou |
| 2011/0091973 A1 | 4/2011 | Glaser |
| 2011/0123561 A1 | 5/2011 | Barrat |
| 2011/0275543 A1 | 11/2011 | Deutsch |
| 2011/0300205 A1 | 12/2011 | Geall |
| 2012/0009140 A1 | 1/2012 | Godfrin |
| 2012/0064505 A1 | 3/2012 | Suresh |
| 2012/0064518 A1 | 3/2012 | Diefenbach |
| 2012/0207745 A1 | 8/2012 | Godfrin |
| 2012/0222143 A1 | 8/2012 | Fahrenkrug |
| 2012/0322157 A1 | 12/2012 | Yohn |
| 2013/0023051 A1 | 1/2013 | Bundock et al. |
| 2013/0065314 A1 | 3/2013 | MacMillan |
| 2014/0287509 A1 | 9/2014 | Sharei et al. |
| 2015/0184127 A1 | 7/2015 | White |
| 2015/0266022 A1 | 9/2015 | Eltoukhy |
| 2016/0083687 A1* | 3/2016 | Sanders ................ C12N 5/00 435/235.1 |
| 2016/0193605 A1 | 7/2016 | Sharei et al. |
| 2016/0324946 A1 | 11/2016 | Godfrin |
| 2017/0020926 A1 | 1/2017 | Mata-fink |
| 2017/0326213 A1 | 11/2017 | Jajosky |
| 2018/0003696 A1 | 1/2018 | Sharei et al. |
| 2018/0016539 A1* | 1/2018 | Ding ..................... C12M 35/04 |
| 2018/0085402 A1 | 3/2018 | Kahvejian |
| 2018/0142198 A1 | 5/2018 | Sharei et al. |
| 2018/0201889 A1 | 7/2018 | Sharei |
| 2018/0344822 A1 | 12/2018 | Godfrin |
| 2018/0361382 A1 | 12/2018 | Zobi |
| 2019/0017072 A1* | 1/2019 | Ditommaso ........... C12M 23/16 |
| 2019/0030536 A1 | 1/2019 | Sharei |
| 2019/0076847 A1 | 3/2019 | Donovan |
| 2019/0093073 A1 | 3/2019 | Sharei |
| 2019/0111082 A1* | 4/2019 | Gilbert .................. C12N 15/85 |
| 2019/0382796 A1* | 12/2019 | Gilbert .................. C12N 15/90 |
| 2020/0316604 A1 | 10/2020 | Dadgar |
| 2021/0138050 A1* | 5/2021 | Loughhead ............. A61P 29/00 |

FOREIGN PATENT DOCUMENTS

| | | |
|---|---|---|
| CN | 102884170 A | 1/2013 |
| CN | 103987836 A | 8/2014 |
| EP | 0414007 A2 | 2/1991 |
| EP | 0882448 A1 | 12/1998 |
| EP | 1225228 A2 | 7/2002 |
| EP | 2169070 A1 | 3/2010 |
| GB | 1051382 A | 12/1966 |
| JP | 01196566 A | 8/1989 |
| JP | 0235081 A | 2/1990 |
| JP | 0253490 A | 2/1990 |
| JP | 03257366 A | 11/1991 |
| JP | 0662867 A | 3/1994 |
| JP | 115752 A | 1/1999 |
| JP | 2005530762 A | 10/2005 |
| JP | 2007501200 A | 1/2007 |
| JP | 2008524237 A | 7/2008 |
| JP | 2010025852 A | 2/2010 |
| JP | 2011163830 A | 8/2011 |
| JP | 2012531909 A | 12/2012 |
| JP | 2014509195 A | 4/2014 |
| JP | 2014533936 A | 12/2014 |
| KR | 20110009422 A | 1/2001 |
| KR | 100891487 B1 | 4/2009 |
| KR | 20140115560 A | 10/2014 |
| KR | 20140134524 A | 11/2014 |
| RU | 2424792 C2 | 7/2011 |
| WO | 1985000748 A1 | 2/1985 |
| WO | 1996013517 A1 | 5/1996 |
| WO | 1997020570 A1 | 6/1997 |
| WO | 1998039027 A2 | 9/1998 |
| WO | 200007630 A1 | 2/2000 |
| WO | 2001088102 A1 | 11/2001 |
| WO | 2002067863 A2 | 9/2002 |
| WO | 2003020039 A1 | 3/2003 |
| WO | 2003064464 A1 | 8/2003 |
| WO | 2003094840 A2 | 11/2003 |
| WO | 2004001424 A1 | 12/2003 |
| WO | 2005060993 A1 | 7/2005 |
| WO | 2006016247 A2 | 2/2006 |
| WO | 2006017954 A1 | 2/2006 |
| WO | 2006066003 A2 | 6/2006 |
| WO | 2006105251 A2 | 10/2006 |
| WO | 2007001677 A2 | 1/2007 |
| WO | 2007067032 A1 | 6/2007 |
| WO | 2007097934 A2 | 8/2007 |
| WO | 2008021465 A2 | 2/2008 |
| WO | 2008129426 A2 | 10/2008 |
| WO | 2008134628 A2 | 11/2008 |
| WO | 2009019317 A1 | 2/2009 |
| WO | 2009056332 A1 | 5/2009 |
| WO | 2010016800 A1 | 2/2010 |
| WO | 2010077290 A1 | 7/2010 |
| WO | 2010129671 A2 | 11/2010 |
| WO | 2010145849 A2 | 12/2010 |
| WO | 2011051346 A1 | 5/2011 |
| WO | 2011119492 A1 | 9/2011 |
| WO | 2012069568 A2 | 5/2012 |
| WO | 2012097450 A1 | 7/2012 |
| WO | 2012118799 A2 | 9/2012 |
| WO | 2012162779 A1 | 12/2012 |
| WO | 2013059343 A1 | 4/2013 |
| WO | WO-2013/059343 A1 | 4/2013 |
| WO | 2013185032 A1 | 12/2013 |
| WO | 2014065596 A1 | 5/2014 |
| WO | 2014120956 A1 | 8/2014 |
| WO | 2014165707 A2 | 10/2014 |
| WO | WO-2015/023982 A1 | 2/2015 |
| WO | 2015153102 A1 | 10/2015 |
| WO | 2015161276 A2 | 10/2015 |
| WO | 2016003485 A1 | 1/2016 |
| WO | WO-2016/070136 A1 | 5/2016 |
| WO | WO-2016/077761 A1 | 5/2016 |
| WO | WO-2016/115179 A1 | 7/2016 |
| WO | 2016183482 A1 | 11/2016 |
| WO | WO-2017/008063 A1 | 1/2017 |
| WO | 2017041051 A1 | 3/2017 |
| WO | WO-2017/041050 A1 | 3/2017 |

(56) References Cited

FOREIGN PATENT DOCUMENTS

| WO | 2017070169 | A1 | 4/2017 |
|---|---|---|---|
| WO | 2017106899 | A2 | 6/2017 |
| WO | 2017117418 | A1 | 7/2017 |
| WO | 2017123644 | A1 | 7/2017 |
| WO | 2017123646 | A1 | 7/2017 |
| WO | WO-2017/123663 | A1 | 7/2017 |
| WO | WO-2017/192785 | A1 | 11/2017 |
| WO | WO-2017/192786 | A1 | 11/2017 |
| WO | 2017210334 | A1 | 12/2017 |
| WO | 2018039084 | A1 | 3/2018 |
| WO | 2018106849 | A1 | 6/2018 |
| WO | 2019113125 | A1 | 6/2019 |
| WO | 2019178005 | A2 | 9/2019 |
| WO | 2019178006 | A2 | 9/2019 |
| WO | 2020072833 | A1 | 4/2020 |
| WO | 2020154696 | A1 | 7/2020 |
| WO | 2020176789 | A1 | 9/2020 |
| WO | 2020210162 | A1 | 10/2020 |

OTHER PUBLICATIONS

Sharei, A. et al. (Nov. 7, 2013). "Cell Squeezing as a Robust, Microfluidic Intracellular Delivery Platform," *Journal of Visulaized Experiments* (81):e50980, 9 pages.

Adamo, A. et al. (Aug. 7, 2012, e-pub. Jul. 10, 2012). "Microfluidics-Based Assessment of Cell Deformability," Anal Chem 84(15):6438-6443.

Adriaenssens, K. et al. (1976). "Use of enzyme-loaded erythrocytes in in-vitro correction of arginase-deficient erythrocytes in familial hyperargininemia," Clin Chem 22(3):323-326.

Albina, J.E. et al. (Apr. 1, 1988). "Arginine Metabolism in Wounds", The American Phvsioloqical Society 254(4):E459-E467. (located at https://journals.physiology.org/doi/pdf/10.1152/ajpendo.1988.254.4.e459, last visited on Aug. 20, 2020).

Ash, David E. (Oct. 2004). "Structure and Function of Arginases", The Journal of Nutrition 134(10):2760S-2764S.

ATCC (2012, Thawing, Propagating, and Cryopreserving Protocol, NCI-PBCF-HTB81 (DU 145) Prostate Carcinoma (ATCCÂ®HTB-81), Version 1.6.

Augustsson et al. (Aug. 28, 2012). "Microfluidic, Label-Free-Enrichment of Prostate Cancer Cells in Blood 4 Based on Acoustophoresis," Analytical Chemistry 84(18):7954-7962.

Bailleul, C. et al. (1991). "Internalization of Various Allosteric Effectors of Hemoglobin in Human Erythrocytes", Advances in the Biosciences 81:9-16.

Banchereau, J. et al. (Aug. 10, 2001). "Dendritic Cells as Vectors for Therapy", Cell 106(3):271-274.

Banz, A. et al. (Jun. 2012). "Tumor Growth Control Using Red Blood Cells as the Antigen Delivery System and Poly (I: C)," J Immunother 35(5):409-417.

Banz, et al. (Aug. 4, 2003). "A Unique Subpopulation of CD4+ Regulatory T Cells Controls Wasting Disease, IL-1 O Secretion and T Cell Homeostasis", Eur. J. Immunol. 33(9):2419-2428.

Bax, B.E. et al. (Feb. 1, 1999). "Survival of Human Carrier Erythrocytes In Vivo", Clinical Science 96(2):171-178.

Bax, B.E. et al. (Jul. 7, 2007). "A 9-yr Evaluation of Carrier Erythrocyte Encapsulated Adenosine Deaminase (ADA) Therapy in a Patient with Adult-Type ADA Deficiency," Eur. J. Haematol 79(4):338-348, 1 page. (Abstract Only).

Bax, B.E. et al. (Jun. 2000). "In Vitro and In Vivo Studies with Human Carrier Erythrocytes Loaded with Polyethylene Glycol-Conjugated and Native Adenosine Deaminase," Br. J. Haematol. 109(3):549-554.

Bigbee, W.L. et al. (Dec. 1983). "Monoclonal Antibodies Specific for the M- and N- Forms of Human Glycophorin A*," Molecular Immunology 20(12):1353-1362.

Boberg, A. et al. (Apr. 18, 2007). "Immunization with HIV Protease Peptides Linked to Syngeneic Erythrocytes", Infectious Agents and Cancer 2(9):1-4.

Bomalaski, J.S. et al. (2003). "Comparative Toxicity of Arginine Deiminase Formulated with Poly(Ethylene Glycol) 5000 or 20,000 and the Effects of Arginine", PreClinica 1(5):284-293.

Bonifaz, L. et al. (Dec. 16, 2002). "Efficient Targeting of Protein Antigen to the Dendritic Cell Receptor DEC-205 in the Steady State Leads to Antigen Presentation on Major Histocompatibility Complex Class I Products and Peripheral CD8+ T Cell Tolerance", J. Exp. Med. 196(12):1627-1638.

Boohaker, J. et al. (Nov. 22, 2012). "The Use of Therapeutic Peptides to Target and to Kill Cancer Cells," Curr Med Chern. 19(22)3794-3804, 26 pages.

Booty, M. (Jan. 2019). "SQZing Cells to Engineer a New Generation of Cancer Vaccines," Power Point Presentation, presented the Keystone: Cancer Vaccine Conference, Vancouver, British Columbia, Canada, Jan. 22, 2019, 16 pages.

Booty, M. et al. (Jan. 2019). "SQZing Cells to Engineer a New Generation of Cancer Vaccines," Poster, presented at the Keystone: Cancer Vaccine Conference, Vancouver, British Columbia, Canada, Jan. 20-24, 2019, 1 page. (Poster).

Booty, M. et al. (Nov. 2018). "SQZ'ing Cells to Engineer Next Generation Antigen Presenting Cell (APC) Therapies," Poster, presented at the Society for Immunotherapy of Cancer's 33rd Annual Meeting, Washington, DC, Nov. 7-11, 2018, 1 page. (Poster).

Boucher, L. et al. (Aug. 1996). "Internalization and Distribution of Inositol Hexakisphosphate in Red Blood Cells", Biotechnology and Applied Biochemistry 24(1):73-78.

Bouvier, M. et al. (2008). "A Novel Approach For A Specific Delivery Of Glucocerebrosidase In Bone Marrow Gaucher Cells," Abstract, Molecular Genetics And Metabolism 93(2):S17, 1 page. (Abstract).

Braner, M. et al. (Dec. 21, 2016). "'Traceless' Tracing Of Proteins-High-Affinity Transsplicing Directed By A Minimal Interaction Pair," Chem. Sci. 7:2646-2652.

Bratosin, D. et al. (2001). "Programmed cell death in mature erythrocytes: a model for investigating death effector pathways operating in the absence of mitochondria," Cell Death Diff. 8:1143-1156.

Breous, E. et al. (Jul. 29, 2009). "Hepatic Regulatory T Cells and Kupffer Cells are Crucial Mediators of Systemic T Cell Tolerance to Antigens Targeting Murine Liver", Hepatoloqy 50(2):612-620.

Bridgen, D. (Dec. 2016). "Topic Category: 801, Gene Therapy and Transfer: Vector Free Genome Editing of Human CD34+ Cells for Cell Therapy," Abstract, presented at 58th American Society of Hematology Annual Meeting, San Diego, California, Dec. 3-6, 2016, 1 page. (Abstract).

Bridgen, D. (Dec. 2016). "Vector Free Genome Editing of Human CD34+ Cells for Cell Therapy," Poster, presented at the 58th American Society of Hematology Annual Meeting, San Diego, California, Dec. 3-6, 2016, 1 page. (Poster).

Bridgen, D. (Mar. 2019). "Mitigating Immune Response to AAV Vectors for Gene Therapy Through Engineered Erythrocytes," Poster, presented at the Antigen-Specific Immune Tolerance Drug Development, Boston, MA, Mar. 26-28, 2019, 1 page. (Poster).

Bridgen, D. (May 2017). "Topic Category: D, Synthetic/Molecular Conjugates and Non-Viral Methods for Delivery of Gene Therapeutics: Vector-Free Genome Editing of Primary Immune Cells for Cell Therapy," Abstract, presented at the 20th American Society of Gene and Cell Therapy Annual Meeting, Washington, D.C, May 10-13, 2017, 1 page. (Abstract).

Bridgen, D. (May 2017). "Vector-Free Genome Editing of Primary Immune Cells for Cell Therapy," Power Point Presentation, presented at the 20th American Society of Gene and Cell Therapy Annual Meeting, Washington, D.C, May 10, 2017, 15 pages.

Bustos, N. et al. (Nov. 30, 1989, Dec. 1989). "Enzyme Replacement Therapy In Porphyrias—V. Ln Vivo Correction Of Delta-Aminolaevulinate Dehydratase Defective In Erythrocytes In Lead Intoxicated Animals by Enzyme-Loaded Red Blood Cell Ghosts," Drug Design And Delivery 5(2):125-131.

Cabantchik, Z.I. et al. (Apr. 8, 1975, e-pub. Feb. 3, 2003). "A Comparison Of Intact Human Red Blood Cells And Resealed And Leaky Ghosts With Respect To Their Interactions With Surface Labelling Agents And Proteolytic Enzymes", Biochim Biophys Acta. 382(4):621-633.

(56) References Cited

OTHER PUBLICATIONS

Cassereau, L. et al. (Apr. 2019). "Tumor-Specific T Cell Engineering for Enhanced Effector Function Via Microfluidic Delivery of Bioactive Molecules," Poster, presented at the American Association of Cancer Research Annual Meeting 2019, Atlanta, GA, Mar. 29-Apr. 3, 2019, 1 page. (Poster).

Cassereau, L. et al. (May 2018). "Mitigating T Cell Response to AAV Vectors for Gene Therapy Through Engineered Red Blood Cells," Poster, presented at the 21st American Society of Gene and Cell Therapy Annual Meeting, Chicago, IL, May 16-19, 2018, 1 page. (Poster).

Chaw, K. et al. (Aug. 2007, e-pub. Jun. 13, 2007). "Multi-Step Microfluidic Device for Studying Cancer Metastasis," Lab Chip 7(8):1041-1047.

Chen, Xian-Zhen et al. (2010, e-pub. Jul. 4, 2009). "Toll Like Receptor Agonists Augment HPV 11 E7-Specific T Cell Responses By Modulating Monocyte-Derived Dendritic Cells", Arch Dermatol Res. 302(1):57-65.

Chow, J. (Jan. 2019). "Enhancing Dendritic Cell Function via mRNA Delivery for Cancer Vaccines," Poster, presented at the Keystone: Cancer Vaccine Conference, Vancouver, British Columbia, Canada, Jan. 20-24, 2019, 1 page. (Poster).

Chow, J. et al. (Jan. 2019). "Enhancing Dendritic Cell Function via mRNA Delivery for Cancer Vaccines," Abstract, presented at the Keystone: Cancer Vaccine Conference, Vancouver, British Columbia, Canada, Jan. 20-24, 2019, 1 page. (Abstract).

Congwu, H. et al. (May 2015). "A Hemicellulose-Bound Form Of Silicon With Potential To Improve The Mechanical Properties And Regeneration Of The Cell Wall Of Rice", The New Phytologist 206(3):1051-1062.

Corinti, S. et al. (Apr. 1, 2002). "Erythrocytes Deliver Tat To Interferon-Gamma-Treated Human Dendritic Cells For Efficient Initiation Of Specific Type 1 Immune Responses In Vitro" Journal Of Leukocyte Biology 71(4):652-658.

Cremel et al. (Aug. 1, 2015, e-pub. Jun. 6, 2015). "Innovative Approach In Pompe Disease Therapy: Induction Of Immune Tolerance By Antigen-Encapsulated Red Blood Cells," Int J Pharm. 491(1-2):69-77.

Cremel et al. (Feb. 25, 2013, e-pub. Jan. 7, 2013). "Red Blood Cells as Innovative Antigen Carrier to Induce Specific Immune Tolerance," Int J Pharm.443(1-2):39-49.

Curley, S.A. et al. (Aug. 31, 2003). "Regression of hepatocellular cancer in a patient treated with arginine deiminase", Hepatogastroenterology 50(53):1214-1216, 1 page. (Abstract Only).

Deleuze, P.H. et al. (Apr. 1, 1992). "Enhanced O2 Transportation During Cardiopulmonary Bypass In Piglets By The Use Of Inositol Hexaphoshate Loaded Red Blood Cells", The International Journal of Artificial Organs 15(4):239-242.

Delorme, E. (Sep. 1989). "Transformation Of *Saccharomyces cerevisiae* By Electroporation," Applied and Environmental Microbiology 55(9):2242-2246.

Didelon, J. et al. (2000). "Osmotic Fragility Of The Erythrocyte Membrane: Characterization By Modeling Of The Transmittance Curve As A Function Of The NaCl Concentration", Biorheology 37(5-6):409-416.

Didelon, J. et al. (2000). "Validation Of A Test Of The Red Cell Membrane Osmotic Resistance", Clinical Hemorheology And Microcirculation 23(1):31-42.

Dillon, B.J. et al. (2002, e-pub. Jul. 15, 2000). "Biochemical Characterization Of The Arginine Degrading Enzymes Arginase And Arginine Deiminase And Their Effect On Nitric Oxide Production", Med. Sci. Monit. 8(7):248-253.

Ding, X. et al. (Mar. 9, 2017). "High-throughput nuclear delivery and rapid expression of DNA via mechanical and electrical cellmembrane disruption," Nature Biomedical Engineering 1(3):39, 15 pages.

Dioun, A. F. et al. (Jul. 1998). "IgE-Mediated Allergy And Desensitization To Factor IX In Hemophilia B", J. Allerqy Clin Immunol. 102(1):113-117.

Ditommaso, T. et al. (Nov. 13, 2018, e-pub. Oct. 31, 2018). "Cell Engineering with Microfluidic Sgueezing Preserves Functionality of Primary Immune Cells in vivo," PNAS 115(46):E10907-E10914, 8 pages.

Dominici, S. et al. (May 16, 2003). "Red Blood Cell-Mediated Delivery of Recombinant HIV-1 Tat Protein in Mice Induces Anti-Tat Neutralizing Antibodies and CTL", Vaccine 21(17-18): 2073-2081.

Dong, V.M. et al. (Jul. 31, 1999). "Transplantation Tolerance: The Concept And Its Applicability", Ped. Transplant. 1993:3:181-192.

Downs, C.A. et al. (Oct. 2011, e-pub. May 14, 2011). "Cell Culture Models Using Rat Primary Alveolar Type I Cells", Pulmornary Pharmacology & Therapeutics 24(5):577-586.

Durand-Smet, P. et al. (Nov. 18, 2014). "A Comparative Mechanical Analysis of Plant and Animal Cells Reveals Convergence across Kingdoms" Biophysical Journal 107(10):2237-2244, 32 pages (includes supplementary material).

Eixarch, H. et al. (May 2009). "Tolerance Induction In Experimental Autoimmune Encephalomyelitis Using Non-Myeloablative Hematopoietic Gene Therapy With Autoantigen," Molecular Therapy 17(5):897-905, 11 pages (includes supplementary material).

Ensor, C. M. et al. (Oct. 2002). "Pegylated Arginine Deiminase (ADI-SS PEG20,000 mw) Inhibits Human Melanomas and Hepatocellular Carcinoma in Vitro and in Vivo", Cancer Research 62(19):5443-5450.

Esposito, F. et al. (Dec. 1, 1990). "Intraerythrocytic Administration of a Synthetic Plasmodium Antigen Elicits Antibody Response in Mice, Without Carrier Molecules or Adjuvants", International Journal Of Parasitology 20(8):1109-1111.

Eymard et al. (2003). "Cell Therapy and Prostate Cancer", Dossier Thematique 90(8-9):734-743.

Fagerlund, R. D. et al. (Dec. 31, 2015). "The Cpf1 CRISPR-Cas Protein Expands Genome-Editing Tools," Genome Biology 16:251, 3 pages.

Favretto et al. (Sep. 28, 2013, e-pub. Jun. 6, 2013). "Human Erythrocytes as Drug Carriers: Loading Efficiency and Side Effects of Hypotonic Dialysis, Chlorpromazine Treatment and Fusion with Liposomes," J Control Release 170(3):343-351.

Gietz, R. et al. (Apr. 2001, e-pub. Sep. 5, 2018). "Genetic Transformation of Yeast," Bio Techniques. 20(4):816-831.

Gong, H. et al. (Apr. 28, 2000). "Arginine Deiminase Inhibits Proliferation Of Human Leukemia Cells More Potently Than Asparaginase By Inducing Cell Cycle Arrest And Apoptosis", Leukemia 14:826-829.

Gong, H. et al. (Sep. 20, 2003, e-pub. Jun. 18, 2003). "Arginine Deiminase And Other Antiangiogenic Agents Inhibit Unfavorable Neuroblastoma Growth: Potentiation By Irradiation", Int. J Cancer. 106(5):723-728.

Griesbeck, M. et al. (2015, e-pub. Oct. 30, 2015). "Sex Differences in Plasmacytoid Dendritic Cell Levels of IRF5 Drive Higher IFN-α Production in Women," J Immunol. 195:5327-5336.

Grimm, A.J. et al. (2015, e-pub. Oct. 29, 2015). "Memory of Tolerance and Induction of Regulatory T Cells by Erythrocyte-Targeted Antigens," Sci Rep. 5:15907, 11 pages.

Hallow D.M. et al. (Mar. 1, 2008, e-pub. Sep. 18, 2007). "Shear-Induced Intracellular Loading of Cells With Molecules by Controlled Microfluidics", Biotechnology and Bioengineering 99(4):846-854.

Hamidi, M. et al. (2003, e-pub. Sep. 29, 2008). "Carrier Erythrocytes: An Overview", Drug Delivery 10(9):9-20.

Hamidi, M. et al. (2007, e-pub. Oct. 10, 2008). "Preparation And Validation Of Carrier Human Erythrocytes Loaded By Bovine Serum Albumin As A Model Antigen/Protein," Drug Delivery 14(5):295-300.

Hamidi, M. et al. (Apr. 2, 2007, e-pub. Dec. 15, 2006). "Applications of Carrier Erythrocytes in Delivery of Biopharmaceuticals," J. Control. Release, 2007, 118(2): 145-160.

Han, X. et al. (Aug. 14, 2015). "CRISPR-Cas9 Delivery To Hard-To-Transfect Cells Via Membrane Deformation," Science Advances 1(7):e1500454, 9 pages.

Hanson, J. (Dec. 2018). "A comparative study elucidating the substantial functional defects of electroporated T cells relative to a mechanical SQZ-based approach," Poster, presented at the Euro-

(56) References Cited

OTHER PUBLICATIONS pean Society for Medical Oncology Immuno-Oncology Congress 2018, Geneva, Switzerland, Dec. 13-16, 2018, 1 page. (Poster).
Hanson, J. (Feb. 2019). "Efficient Genome Engineering Using Microfluidic Delivery of Bioactive Molecules via the SQZ Platform," Power Point Presentation, presented at the Keystone: Genome Engineering: From Mechanisms to Therapies Conference, Victoria, British Columbia, Canada, Feb. 23, 2019, 14 pages.
Hanson, J. (May 2018). "Efficient Genome Editing of Immune Cells Using Microfluidic Delivery as a Novel Approach to Cell Therapy," Poster, presented at the 21st American Society of Gene and Cell Therapy Annual Meeting, Chicago, IL, May 16-19, 2018, 1 page. (Poster).
He, C. et al. (May 2015). "A Hemicellulose-Bound Form Of Silicon With Potential To Improve The Mechanical Properties And Regeneration Of The Cell Wall Of Rice," New Phytologist 206(3):1051-1062.
Hervas-Stubbs, S. et al. (Jun. 15, 2007, Mar. 5, 2007). "TLR3 ligand stimulates fully functional memory—CD8+T cells in the absence of CD4+ T-cell help," Immunobiology 109(12):5318-5326.
Hillerdal, V. et al. (Jan. 18, 2014). "Systemic Treatment With CAR-engineered T Cells Against PSCA Delays Subcutaneous Tumor Growth And Prolongs Survival Of Mice," BMC Cancer 14(30):1-9.
Hlavarty, K. et al. (Apr. 2019). "Engineering a New Generation of Cell Therapies for Solid Tumor Oncology using the SQZ Platform," Poster, presented at the American Association of Cancer Research Annual Meeting 2019, Atlanta, GA, Mar. 29-Apr. 3, 2019, 1 page. (Poster).
Hlavaty, K. et al. (Feb. 2018). "Engineering T Cells Using a Microfluidic Intracellular Delivery Method for Cell Therapy," Poster, presented at the Keystone: Emerging Cellular Therapies—T Cells and Beyond Conference, Keystone, CO, Feb. 11-15, 2018, 1 page. (Poster).
Hlavaty, K. et al. (Feb. 2018). "Engineering T Cells Using a Microfluidic Intracellular Delivery Method for Cell Therapy," Power Point Presentation, presented at the Keystone: Emerging Cellular Therapies—T Cells and Beyond Conference, Keystone, CO, Feb. 12, 2018, 15 pages.
Hoeppener, A.E.L.M. (2012, e-pub. Apr. 21, 2012). "Immunomagnetic Separation Technologies," Recent Results in Cancer Research 195:43-58.
Holtsberg, F.W. et al. (Apr. 23, 2002). "Poly(ethylene glycol) (PEG) Conjugated Arginine Deiminase: Effects Of PEG Formulations On Its Pharmacological Properties," Journal of Controlled 80(1-3):259-271.
Hoskin, D.W. et al. (Feb. 2008, e-pub. Nov. 22, 2007). "Studies On Anticancer Activities Of Antimicrobial Peptides," Biochimica et Biophysica Acta 1778(2):357-375.
Hosokawa, M. et al. (Aug. 1, 2010). "Size-Selective Microcavity Array for Rapid and Efficient Detection of Circulating Tumor Cells", Analytical Chemistry 82(15):6629-6635.
Hussain, A.A. et al. (Aug. 1984). "Erythrocyte Osmotic Fragility in Man: Variation with Age and Sex", Br. J. Haematol. 57(4):716-718.
Indrova, M. et al. (Jan. 1, 2004). "Immunogenicity of Dendritic Cell-Based HPV16 E6/E7 Peptide Vaccines: CTL Activation and Protective Effects", Folia Biologica 50:184-193.
Ing, R. et al. (Jan. 1, 2006). "Interaction-of Mouse Dendritic Cells and Malaria-Infected Erythrocytes: Uptake, Maturation, and Antigen Presentation," Journal of immunology 176(1):441-450.
International Preliminary Report on Patentability dated Apr. 22, 2014, for International Patent Application No. PCT/US2012/060646, filed Oct. 17, 2012, 7 pages.
International Preliminary Report on Patentability dated Feb. 16, 2016, for International Patent Application No. PCT/US2014/051343, filed Aug. 15, 2014, 6 pages.
International Preliminary Report on Patentability dated Feb. 9, 2010, for International Patent Application No. PCT/EP2008/060492, filed Aug. 8, 2008, 7 pages.
International Preliminary Report on Patentability dated Jan. 9, 2018, for International Patent Application No. PCT/US2016/041653, filed Jul. 8, 2016, 8 pages.
International Preliminary Report on Patentability dated Jul. 18, 2017, for International Patent Application No. PCT/US2014/051343, filed Jan. 12, 2016, 6 pages.
International Preliminary Report on Patentability dated Jun. 18, 2020, for International Patent Application No. PCT/US2018/063931, filed Dec. 4, 2018, 9 pages.
International Preliminary Report on Patentability dated Jun. 23, 2020, for International Patent Application No. PCT/US2018/066295, filed Dec. 18, 2018, 15 pages.
International Preliminary Report on Patentability dated Mar. 6, 2018, for International Patent Application No. PCT/US2016/050288, filed Sep. 2, 2016, 8 pages.
International Preliminary Report on Patentability dated May 16, 2017, for International Patent Application No. PCT/US2015/060689, filed Nov. 13, 2015, 10 pages.
International Preliminary Report on Patentability dated May 2, 2017, for International Patent Application No. PCT/US2015/058489, filed Oct. 30, 2015, 12 pages.
International Preliminary Report on Patentability dated Nov. 6, 2018, for International Patent Application No. PCT/US2017/030932 filed May 3, 2017, 9 pages.
International Preliminary Report on Patentability dated Nov. 6, 2018, for International Patent Application No. PCT/US2017/030933, filed May 3, 2017, 12 pages.
International Search Report and Written Opinion of the International Searching Authority dated Apr. 16, 2020, for International Patent Application No. PCT/US2020/020194, 16 pages.
International Search Report and Written Opinion of the International Searching Authority dated Apr. 20, 2020, for International Patent Application No. PCT/US2020/015098, filed Jan. 24, 2020, 17 pages.
International Search Report and Written Opinion of the International Searching Authority dated Dec. 1, 2016, for International Patent Application No. PCT/US2016/050288, filed Sep. 2, 2016, 11 pages.
International Search Report and Written Opinion of the International Searching Authority dated Feb. 25, 2013, for International Patent Application No. PCT/US12/060646, filed Oct. 17, 2012, 10 pages.
International Search Report and Written Opinion of the International Searching Authority dated Jan. 3, 2017, for PCT Patent Application No. PCT/US2016/050287, filed Sep. 2, 2016, 10 pages.
International Search Report and Written Opinion of the International Searching Authority dated Jul. 21, 2017 for International Patent Application No. PCT/US2017/030933, filed May 3, 2017, 15 pages.
International Search Report and Written Opinion of the International Searching Authority dated Mar. 19, 2019, for International Patent Application No. PCT/US2018/063931, filed Dec. 14, 2018, 14 pages.
International Search Report and Written Opinion of the International Searching Authority dated Mar. 27, 2020, for International Patent Application No. PCT/US2018/066295, filed Dec. 18, 2018, 23 pages.
International Search Report and Written Opinion of the International Searching Authority dated Oct. 16, 2019 for International Patent Application No. PCT/US2019/021705, filed Mar. 11, 2019, 25 pages.
International Search Report and Written Opinion of the International Searching Authority dated Oct. 4, 2016, for International Application No. PCT/US2016/041653, filed Jul. 8, 2016, 10 pages.
International Search Report and Written Opinion of the International Searching Authority dated Dec. 18, 2014, for International Patent Application No. PCT/US2014/051343, filed Aug. 15, 2014, 7 pages.
International Search Report and Written Opinion of the International Searching Authority dated Feb. 1, 2016, for International Patent Application No. PCT/US2015/060689, filed Nov. 13, 2015, 12 pages.

(56) References Cited

OTHER PUBLICATIONS

International Search Report and Written Opinion of the International Searching Authority dated Mar. 11, 2016, for International Patent Application No. PCT/US2015/058489, filed Oct. 30, 2015, 18 pages.
International Search Report and Written Opinion of the International Searching Authority dated Mar. 21, 2016, for International Patent Application No. PCT/US2016/013113, filed Jan. 12, 2016, 10 pages.
International Search Report and Written Opinion of the International Searching Authority dated Oct. 1, 2008, for International Patent Application No. PCT/EP2008/060492, filed Aug. 8, 2008, 10 pages.
International Search Report and Written Opinion of the International Searching Authority dated Sep. 18, 2019, for International Patent Application No. PCT/US2019/021703, filed Mar. 11, 2019, 19 pages.
International Search Report and Written Opinion of the International Searching Authority dated Sep. 19, 2017 for International Patent Application No. PCT/US2017/030932, filed May 3, 2017, 14 pages.
International Search Report and Written Opinion of the Searching Authority dated Feb. 12, 2020, for International Patent Application No. PCT/US2019/054586, filed Oct. 3, 2019, 27 pages.
Invitation to Pay Additional Fees dated Dec. 19, 2019, for International Patent Application No. PCT/US2019/054586, filed Oct. 3, 2019, 8 pages.
Invitation to Pay Additional Fees dated Jul. 23, 2020, for International Patent Application No. PCT/US2020/026891, filed Apr. 6, 2020, 14 pages.
Invitation to Pay Additional Fees dated Jul. 24, 2019, for International Patent Application No. PCT/US2019/021703, filed Mar. 11, 2019, 14 pages.
Invitation to Pay Additional Fees dated Jun. 28, 2019, for International Patent Application No. PCT/US2019/021705, filed Mar. 11, 2019, 17 pages.
Izzo, F. et al. (May 15, 2004). "Pegylated Arginine Deiminase Treatment of Patients With Unresectable Hepatocellular Carcinoma: Results From Phase 1/11 Studies", Journal Of Clinical Oncology 22(10):1815-1822.
Jordan, J.A. et al. (1999). "Band-3 Crosslinking-Induced Targeting Of Mouse Carrier Erythrocytes," Biotechnol. Appl. Biochem. 29:59-65.
Jordan, J.A. et al. (Jan. 1997, e-pub. Mar. 5, 2000). "In Vitro Properties And Organ Uptake Of Rat Band 3 Cross-Linked Erythrocytes," Biochimie. 79(1):53-61. (p. 1 Only).
Ju, C. et al. (Apr. 15, 2005, e-pub. Jan. 29, 2005). "Tolerogenic Role Of Kupffer Cells In Immune-Mediated Adverse Drug Reactions", Toxicology 209(2):109-112.
Ju, C. et al. (Dec. 1, 2003, e-pub. Nov. 8, 2003). "Tolerogenic Role of Kupffer Cells in Allergic Reactions", Chem. Res. Taxicol. 16(12):1514-1519.
Kaka, A. S. et al. (Sep. 1, 2009). Genetic Modification of T Cells With IL-21 Enhances Antigen Presentation and Generation of Central Memory Tumor-specific Cytotoxic T-lymphocytes, Journal of Immunology 32(7):726-736.
Kamei, T. et al. (May 1990, e-pub. Feb. 9, 2004). "Kupffer Cell Blockade Prevents Induction of Portal Venous Tolerance in Rat Cardiac Allograft Transplantation", Journal Of Surgical Research 48(5):393-396.
Kenter, G. G. et al. (Nov. 5, 2009). "Vaccination against HPV-16 Oncoproteins for Vulvar Intraepithelial Neoplasia", The New England Journal Of Medicine 361(19):1838-1847, 14 pages. (Including Supplemental Material).
Kiani, S. et al. (Nov. 2015, e-pub. Sep. 7, 2015). "Cas9 gRNA Engineering for Genome Editing, Activation and Repression", Nature Methods 12(11):1051-1054.
Klein, A. et al. (Aug. 20, 2018). "Live-Cell Labeling of Endogenous Proteins with Nanometer Precision by Transduced Nanobodies," Chem. Sci. 9:7835-7842.
Kolanjiappan, K. et al. (Dec. 2002, e-pub. Oct. 28, 2002). "Measurement Of Erythrocyte Lipids, Lipid Peroxidation, Antioxidants And Osmotic Fragility In Cervical Cancer Patients", Clinica Chimic Acta 326(1-2):143-149.
Kollmannsperger, A. et al. (Jan. 29, 2016). "Live-Cell Protein Labelling With Nanometre Precision By Cell Squeezing," Nat Comm 7(10372):1-7.
Kontos, S. et al. (Jan. 2, 2013, e-pub. Dec. 17, 2012). "Engineering antigens for in Situ Erythrocyte Binding Induces T-cell Deletion," PNAS USA. 110(1):E60-E68.
Kravtzoff, R. et al. (Jul. 1990). "Erythrocytes As Carriers For L-Asparaginase Methodological And Mouse In-Vivo Studies", The Journal Of Pharmacy And Pharmacology 42(7):473-476.
Kwon, Y.M. et al. (Nov. 3, 2009, e-pub. Jul. 3, 2009). "L-Asparaginase Encapsulated Intact Erythrocytes For Treatment Of Acute Lymphoblastic Leukemia (ALL)" Journal of Controlled Release 139(3):182-189.
Lange, P.S. et al. (Oct. 2004). "Novel Roles for Arginase in Cell Survival, Regeneration, and Translation in the Central Nervous System," The Journal of Nutrition (Arginase In The Central Nervous System) 134(10):2812S-2817S.
Lau, A.H. et al. (2003, e-pub. Jul. 15, 2003). "Liver Tolerance Mediated By Antigen Presenting Cells: Fact Or Fiction?," Gut 52(8):1075-1078.
Lee, J. (Nov. 16, 2012, e-pub. Dec. 2012). "Non-Endocytic Delivery Of Functional Engineered Nanoparticles Into The Cytoplasm Of Live Cells Using A Novel, High-Throughput Microfluidic Device," Nano Lett. 12(12):6322-6327.
Lee, T. et al. (Apr. 2019). "Engineering Erythrocytes with the SQZ Cell Therapy Platform to Enhance Immuno-Tolerance," Abstract, presented at the Rachmiel Levine-Arthur Riggs Diabetes Research Symposium 2019 Conference, Pasadena, CA, Apr. 10-13, 2019, 1 page. (Abstract).
Lee, T. et al. (Apr. 2019). "Engineering Erythrocytes with the SQZ Cell Therapy Platform to Enhance Immuno-Tolerance," Poster, presented at the Rachmiel Levine-Arthur Riggs Diabetes Research Symposium 2019 Conference, Pasadena, CA, Apr. 10-13, 2019, 1 page. (Poster).
Lee, T. et al. (Feb. 2019). "Engineering Erythrocytes with the SQZ Cell Therapy Platform to Enhance Immuno-Tolerance," Poster, presented at the Keystone: Uncovering Mechanisms of Immune-Based Therapy in Cancer and Autoimmunity Conference, Breckenridge, CO, Feb. 18-22, 2019, 1 page. (Poster).
Li, J. et al. (Dec. 15, 2017). "Microfluidic-Enabled Intracellular Delivery of Membrane Impermeable Inhibitors to Study Target Engagement in Human Primary Cells," ACS Chemical Biology 12(12):2970-2974.
Li, J. et al. (Jun. 30, 2016, May 19, 2016). "The Combination Of Pleurotus Ferulaewater Extract And CpG-ODN Enhances The Immune Responses And Antitumor Efficacy Of HPV Peptides Pulsed Dendritic Cell-Based Vaccine", Vaccine 34(31):3568-3575.
Liang, X. et al. (Aug. 20, 2015, e-pub. May 21, 2015). "Rapid and Highly Efficient Mammalian Cell Engineering via Cas9 Protein Transfection", J. Biotech 208:44-53.
Limmer, A. et al. (Dec. 2000). "Efficient presentation of exogenous antigen by liver endothelial cells to CD8+ T cells results in antigen-specific T-cell tolerance", Nature Medicine 6(12):1348-1354.
Lin et al. (Jun. 26, 2013). "Highly selective biomechanical separation of cancer cells from leukocytes using 1-19 microfluidic ratchets and hydrodynamic concentrator," Biomicrofluidics 7(3):1-11.
Lind, D. S. (2004). "Arginine Metabolism: Enzymology, Nutrition, and Clinical Significance: Arginine and Cancer1," J. Nutr. 134:2837S-2841S.
Liu et al. (2014, Jul. 28, 2014). "Molecular Imaging In Tracking Tumor-Specific Cytotoxic T Lymphocytes (CTLs)," Theranostics 4(10):990-1001.
Liu, Y. et al. (Sep. 19, 2012, e-pub. Jul. 13, 2012). "Spatially selective reagent delivery into cancer cells using a two-layer microfluidic culture system," Anal Chim Acta 743(1):125-130.
Lorentz et al. (Jul. 2015, e-pub. Jul. 17, 2015). "Engineered Binding to Erythrocytes Induces Immunological Tolerance to E. coli Asparaginase," Sci Adv. 1(6):e1500112, 11 pages.

(56) References Cited

OTHER PUBLICATIONS

Lou, Y. et al. (Feb. 1, 2007). "Plasmacytoid Dendritic Cells Synergize with Myeloid Dendritic Cells in the Induction of Antigen-Specific Antitumor Immune Responses", The Journal of Immunology 178(3):1534-1541.

Loughhead, S. et al. (Dec. 2018). "SQZing Cells to Rapidly Generate Autologous Antigen Presenting Cells for Solid Tumor Immune Therapies with Efficient, Scalable Manufacturing," Poster, presented at the European Society for Medical Oncology Immuno-Oncology Congress 2018, Geneva, Switzerland, Dec. 13-16, 2018, 1 page. (Poster).

Loughhead, S.M. et al. (Dec. 1, 2018). "SQZing Cells To Rapidly Generate Antigen Presenting Cells (APC) For Solid Tumor Immune Therapies With Efficient, Scalable Manufacturing," Annals Of Oncology 29(Suppl No. 10):1page, (Abstract No. 38P). (Abstract).

Mahnke, K. et al. (Jun. 15, 2003). "Induction of CD4+/CD25+ Regulatory T Cells By Targeting Of Antigens To Immature Dendritic Cells," Blood 101(12):4862-4869.

Mali, P. et al. (Feb. 15, 2013, e-pub. Jan. 3, 2013). "RNA Guided Human Genome Engineering via Cas9," Science 339(6121):823-826.

Maratou, E. et al. (Apr. 2007). "Glucose Transporter Expression On The Plasma Membrane Of Resting And Activated White Blood Cells," Eur J Clin Invest 37(4):282-290.

Marketletter (Sep. 13, 1999). "Autoimmune Shares Collapse on Colloral Data in Rheumatoid Arthritis," Marketletter Pubs Ltd. (UK), Newsletter. (ISSN:0951-3175) 2 pages.

Marx, V. (Jan. 2016, e-pub. Dec. 30, 2015). "Cell Biology: Delivering Tough Cargo into Cells," Nature Methods 13(1):37-40.

Matsui, H. et al. (Jul. 16, 2009, e-pub. May 20, 2009). "A Murine Model For Induction Of Long-Term Immunologic Tolerance To Factor VIII Does Not Require Persistent Detectable Levels Of Plasma Factor VIII And Involves Contributions From Foxp3+ T Regulatory Cells," Blood (Thrombosis and Hemostasis) 114(3):677-685.

McCarthy, D. (Oct. 2018). "Engineering Erythrocytes for Immune Tolerance via CellSqueeze® Technology," Poster, presented at the Immunology of Diabetes Society Congress, London, UK, Oct. 25-29, 2018, 1 page.

Miao, C. H. et al. (Nov. 5, 2009, e-pub. Aug. 27, 2009). "CD4+ FOXP3+ Regulatory T Cells Confer Long-Term Regulation Of Factor VI II-Specific Immune Responses In Plasmid-Mediated Gene Therapy-Treated Hemophilia Mice," Blood 114(19):4034-4044.

Millan, C.G. et al. (Feb. 20, 2004, e-pub. Feb. 25, 2004). "Drug Enzyme And Peptide Delivery Using Erythrocytes As Carriers", Journal Of Controlled Release 95(1):27-49.

Milo, R. et al. (Sep. 20, 2013). "What Is The Total Number Of Protein Molecules Per Cell Volume? A Call To Rethink Some Published Values," Bioessays 35(12):1050-1055.

Mori, M. et al. (Oct. 2004). "Arginine Metabolic Enzymes, Nitric Oxide and Infection," The Journal of Nutrition 134(10):2820S-2825S.

Moser, B. et al. (Jul. 2011, e-pub. May 15, 2011). "gamma delta T-APCs: A Novel Tool For Immunotherapy?," Cellular And Molecular Life Sciences 68(14):2443 2452.

Murray, A. M. et al. (Aug. 28, 2006, e-pub. May 23, 2006). "The Mouse Immune Response To Carrier Erythrocyte Entrapped Antigens," Vaccine 24(35-36):6129-6139.

Myint, M. et al. (Jun. 2018). "SQZing Dendritic Cells to Shortcut Cross-Presentation and Enhance CD8+ T Cell Responses for Adoptive Immunotherapies," Poster, presented at the 15th International Symposium on Dendritic Cells (DC 2018), Aachen, Germany, Jun. 10-14, 2018, 1 page. (Poster).

Noblitt, S. D. et al. (Aug. 1-15, 2007, e-pub. Jul. 18, 2007). "Integrated Membrane Filters for Minimizing Hydrodynamic Flowing and Filtering in Microfluidic Devices," Analytical Chemistry 79(16): 6249-6254.

Park, I.S. et al. (Sep. 1, 2003, e-pub. Aug. 26, 2003). "Arginine Deiminase: A Potential Inhibitor Of Angiogenesis And Tumour Growth," Br J. Cancer 89(5):907-914.

Patel, K. et al. (Dec. 1, 2016). "Combination Immunotherapy with NY-ESO-1-Specific CAR+ T Cells with T-Cell Vaccine Improves Anti-Myeloma Effect," Blood Journal 128(22):3366, 1 page (Poster).

Patel, K. et al. (Dec. 1, 2016). "Combination Immunotherapy with NY-ESO-1 -Specific CAR+ T Cells with T-Cell Vaccine Improves Anti-Myeloma Effect," Blood Journal 128(22):3366, 2 pages (Abstract).

Polvani, C. et al. (Dec. 1, 1991). "Murine Red Blood Cells As Efficient Carriers Of Three Bacterial Antigens For The Production Of Specific And Neutralizing Antibodies", Biotechnology And Applied Biochemistry 14:347-356.

Pozzilli, P. et al. (Aug. 2000). "No effect of oral insulin on residual beta-cell function in recent-onset Type I diabetes (the IMDIAB VII)," Diabetol. 43:1000-1004.

Provotorov, V.M. et al. (Dec. 31, 2008). "The Role Of Erythrocytes In The System Of Controlled Transport Of Pharmaceutical Agents", Klin Med. 87(9):4-8, 2 pages. (Abstract Only).

Ravilla, S. et al. (Apr. 28, 2012). : "Erythrocytes as Carrier for Drugs, Enzymes and Peptides", Journal Of Applied Pharmaceutical Science 2(4):166-176.

Regnaul, T. et al. (Jan. 18, 1999). "Fey Receptor-Mediated Induction of Dendritic Cell Maturation and Major Histocompatibility Complex Class I-restricted Antigen Presentation after Immune Complex Internalization," J. Exp. Med. 189(2):371-380.

Ropars, C. et al. (Jul. 1998). "Engineered Erythrocytes: Influence Of P50 Rightward Shift And Oxemia On Oxygen Transport To Tissues," Med. Biol. Eng. Comp. 36:508-512.

Rossi, L. et al. (Nov. 28, 2014, e-pub. Aug. 23, 2014). "Erythrocyte-Mediated Delivery of Phenylalanine Ammonia Lyase for the Treatment of Phenylketonuria in BTBR-Pahenu2 Mice," J Control Release 194:37-44.

Rutella, S. et al. (Sep. 1, 2006). "Tolerogenic Dendritic Cells: Cytokine Modulation Comes of Age", Blood 180(5):1435-1440.

Sadahiro, S. et al. (Aug. 2003). "Pharmacokinetics of 5-Fluorouracil Following Hepatic Intra-arterial Infusion in a VX2 Hepatic Metastasis Model," Japanese J. Clin Oncol. 33(8):377-381.

Sauer, S. et al. (Mar. 2017). "Vector-Free Intracellular Delivery of Small Molecules and Biological Macromolecules for Target Validation and Gene Editing," Poster, presented at Keystone: Engineered Cells and Tissue as Platforms for Discovery and Therapy Conference, Boston, MA, Mar. 9-12, 2017, 1 page. (Poster).

Saung, M. (2016). "A Size-Selective Intracellular Delivery Platform," Small 12(42):5873-5881.

Schrijvers, D. et al. (Aug. 2003, Sep. 13, 2003). "Role of Red Blood Cells in Pharmacokinetics of Chemotherapeutic Agents," Clin. Pharmacokinet 42(9):779-791.

Seeman, P. (Jan. 1, 1967). "Transient Holes in the Erythrocyte Membrane During Hypotonic Hemolysis and Stable Holes in the Membrane After Lysis by Saponin and Lysolecithin," Journal of Cell Biology 32(1):55-70.

Serafini, S. et al. (2004). "Drug Delivery Through Phagocytosis Of Red Blood Cells," Transfus Med Hemother. 31(2):92-101.

Sharei, A. (Jun. 26, 2013). "Cell Squeezing: A Vector-Free Microfluidic Platform for Intracellular Delivery of Macromolecules," MIT Thesis (Public, located here: https://dspace.mit.edu/bitstream/handle/1721.1/81688/860804208-MIT.pdf?sequence=2) 165 pages.

Sharei, A. et al. (Apr. 1, 2014). "Plasma Me,brane Recovery Kinetics of a Microfluioic Intracellular Delivery Platform," Integrative Biology 6(4):470-475.

Sharei, A. et al. (Apr. 13, 2015). "Ex Vivo Cytosolic Delivery of Functional Macromolecules to Immune Cells", PLOS ONE 10(4):e0118803, 12 pages.

Sharei, A. et al. (Jan. 1, 2012). "(483d) Microfluidic Cell Deformation As a Robust, Vector-Free Method for Cytosolic Delivery of Macromolecules," 12AIChE Proceedings, AIChE Annual Meeting, 8 pages.

Sharei, A. et al. (Jan. 22, 2013). "A Vector-Free Microfluidic Platform for Intracellular Delivery," Proceedings of the National Academy of Sciences 110(6):2082-2087.

(56) References Cited

OTHER PUBLICATIONS

Sharei, A. et al. (Nov. 7, 2013). "Cell Squeezing as a Robust, Microfluidic Intracellular Delivery Platform," Journal of Visualized Experiments (81):e50980, 9 pages.

Shelby et al. (Dec. 9, 2003). "A Microfluidic Model for Single-Cell Capillary Obstruction by Plasmodium 51, 53 Falciparum Infected Erythrocytes," PNAS 100(25):14618-14622.

Song et al. (2006). "Scientific Basis for the Use of Hypotonic Solutions with Ultrasonic Liposuction," Aesth. Plast. Surg. 30:233-238.

Spector, E.B. et al. (Nov. 1985). "Comparison or Arginase Activity in Red Blood Cells of Lower Mammals, Primates, and Man: Evolution to High Activity in Primates," Am. J. Hum. Genet. 37(6):1138-1145.

Steinman, R.M. et al. (Apr. 1, 2003). "Tolerogenic Dendritic Cells", Annu. Rev. Immunol. 21:685-711.

Stevenson, D. et al. (e-pub. Jan. 11, 2010). "Single Cell Optical Transfection," Ferroelectrics and Frequency Control 53(1):863-871.

Stewart, M. et al. (Aug. 22, 2018, e-pub. Jul. 27, 2018). "Intracellular Delivery by Membrane Disruption Mechanisms, Strategies, and Concepts," Chem. Rev. 118(16):7409-7531.

Stewart, M.P. et al. (Oct. 12, 2016). "In Vitro and Ex Vitro Strategies for Intracellular Delivery", Nature 538(7624):183-192, 23 pages.

Stuehr, D.J. (Oct. 2004). "Enzymes of the L-Arginine to Nitric Oxide Pathway", The Journal of Nutritional 134(10):2748S-2751S.

Swaminathan, V et al. (Aug. 1, 2011). Mechanical Stiffness Grades Metastatic Potential in Patient Tumor Cells and in Cancer Cell Lines, Cancer Research 71(5):5075-5080.

Szeto, G. et al. (May 22, 2015). "Microfluidic Squeezing for Intracellular Antigen Loading in Polyclonal B-Cells as Cellular Vaccines," Scientific Reports 5:10276, 13 pages.

Tacken, P. J. et al. (Oct. 2007, e-pub. Sep. 14, 2007). "Dendritic-cell immunotherapy: from ex vivo loading to in vivo targeting," Nature Reviews 7:790-802.

Talarico, L. et al. (Nov. 2017). "Engineered Antigen Presenting T Cells for the Treatment of Solid Tumor Cancers," EMBASE, 32nd Annual Meeting and Pre-Conference Programs of the Society for Immunotherapy of Cancer, SITC 2017, Journal for ImmunoTherapy of Cancer 5(Suppl. 2):EMB-619371158, 1 page. (Abstract).

Talarico, L. et al. (Sep. 2018). "Engineered Antigen Presenting T Cells for the Treatment of Solid Tumor Cancers," Cancer Immunol Res 6(9 Suppl.):A61, 5 pages. (Abstract).

Tanchot, C. et al. (2004). "Immune Regulation by Self-Reactive T Cells is Antigen Specific," The Journal of Immuno 172:4285-4291.

Thomas, J. B. et al. (Apr. 24, 2002). "Enzymic Degradation Of Plasma Arginine Using Arginine Deiminase Inhibits Nitric Oxide Production And Protects Mice From The Lethal Effects Of Tumour Necrosis Factor And Endotoxin", Biochem J. 363(3):581-587.

Thornton, A. M. et al. (Jan. 1, 2000). "Suppressor Effector Function of CD4+ CD25+ Immunoregulatory T Cells Is Antigen Nonspecific," Journal of Immunology 164(1):183-190.

Tlaxca, J. et al. (Nov. 1, 2010). Analysis of In Vitro Transfection by Sonoporation Using Cationic and Neutral Microbubbles, Ultrasound Med and Bio 36(11):1907-1918.

Tran, D.Q. et al. (May 2009, e-pub. Feb. 21, 2009). "Therapeutic Potential of FOXP3+ Regulatory T Cells And Their interactions with dendritic cells," Human Immunology 70(5):294-299.

Tsaoir, C. et al. (Jun. 2016). "Scalable Antibody Production from CHO Cell Line of Choice Using Flow Electroporation," Poster, Cell Line Development Jun. 2016, © 2016 MaxCyte, Inc., located at: https://www.maxcyte.com/wp-content/uploads/2017/10/scalable-ab-production-from-cho-cells.pdf, last retrieved on Apr. 2, 2019, 1 page. (Poster).

Tsukamoto, H. et al. (Dec. 1, 1999). "Iron Primes Hepatic Macrophages For NF-Kappab Activation In Alcoholic Liver Injury", Am .J Physiol. 277(6):G1240-G1250.

Tu, C. et al. (May 16, 2016, e-pub. Mar. 9, 2016). "Monitoring Protein Synthesis in Single Live Cancer Cells," Integr Biol (Camb) 8(5):645-653.

Turley, D.M. et al. (2010, e-pub. 2009). "Prospects for Antigen-Specific Tolerance Based Therapies for the Treatment of Multiple Sclerosis," (Molecular Basis of Multiple Sclerosis) Results Probl. Cell Differ. 51:217-235.

U.S. Appl. No. 16/098,405, filed Nov. 1, 2018, by Loughhead et al. (A copy not submitted herewith pursuant to the waiver of 37 C.F.R. § 1.98(a)(2)(iii) issued by the Office on Sep. 21, 2004.).

U.S. Appl. No. 16/141,107, filed Sep. 25, 2018, by Sharei et al. (U.S. Patent Application is not submitted herewith pursuant to the waiver of 37 C.F.R. § 1.98(a)(2)(iii) issued by the Office on Sep. 21, 2004.).

U.S. Appl. No. 16/769,993, filed Dec. 4, 2018, by Sharei et al. (U.S. Patent Application is not submitted herewith pursuant to the waiver of 37 C.F.R. § 1.98(a)(2)(iii) issued by the Office on Sep. 21, 2004.).

U.S. Appl. No. 16/803,937, filed Apr. 6, 2020, by Sharei et al. (U.S. Patent Application is not submitted herewith pursuant to the waiver of 37 C.F.R. § 1,98(a)(2)(iii) issued by the Office on Sep. 21, 2004.).

U.S. Appl. No. 16/818,021, filed Mar. 13, 2020, by Sharei et al. (U.S. Patent Application is not submitted herewith pursuant to the waiver of 37 C.F.R. § 1.98(a)(2)(iii) issued by the Office on Sep. 21, 2004.).

U.S. Appl. No. 16/841,287, filed Apr. 6, 2020, by Maisam et al. (U.S. Patent Application is not submitted herewith pursuant to the waiver of 37 C.F.R. § 1.98(a)(2)(iii) issued by the Office on Sep. 21, 2004.).

U.S. Appl. No. 16/954,113, filed Dec. 18, 2018, by Maisam et al. (U.S. Patent Application is not submitted herewith pursuant to the waiver of 37 C.F.R. § 1.98(a)(2)(iii) issued by the Office on Sep. 21, 2004.).

Van Broeckhoven et al. (Dec. 23, 1982). "Measurement of Arginine Transport in Human Erythrocytes Using Their Intrinsic Arginase Activity: Implications for the Treatment of Familial Hyperargininemia," Clinica Chimica Acta 126(3):209-216.

Van Schooten, W.C. et al. (Jun. 1997, e-pub. Feb. 4, 1998). "Biological Properties of Dendritic Cells Implications to Their Use in the Treatment of Cancer", Molecular Medicine Today 3(6):254-260.

Vellard, M. (Aug. 2003, e-pub. Jun. 24, 2003). "The Enzyme As Drug: Application Of Enzymes As Pharmaceuticals," Current Opinion in Biotechnology 14(4):444-450.

Verma, R. R. et al. (Nov. 2013, e-pub. Sep. 6, 2013). "E6 protein of human papillomavirus 16 (HPV16) expressed in *Escherichia coli* sans a stretch of hydrophobic amino acids, enables purification of GST-[Delta]E6 in the soluble form and retains the binding ability to p53," Protein Expression And Purification 92(1):41-47.

Vicente-Suarez, A. (Apr. 2019). "Engineering Erythrocytes with the SQZ Cell Therapy Platform to Enhance Immuno-Tolerance," Poster, presented at the 13th World Immune Regulation Meeting Conference, Davos, Switzerland, Apr. 6-9, 2019, 1 page. (Poster).

Villa, C.et al. (Dec. 2016, e-pub. Oct. 31, 2016). "Drug Delivery By Erythrocytes: "Primum non Nocere"," Transfusion And Apheresis Science 55(3):275-280.

Wang, B. et al. (Aug. 1, 2003, e-pub. Jul. 29, 2003). "Evaluation of immunologic crossreaction of antiasparaginase antibodies in acute lymphoblastic leukemia (ALL) and lymphoma patients," 17:1583-1588.

Wang, H.L. et al. (Jan. 2014, e-pub. Aug. 3, 2013). "In Vitro And In Vivo Evaluations Of Human Papillomavirus Type 16 (HPV16)-Derived Peptide-Loaded Dendritic Cells (DCs) With A CpG oligodeoxynucleotide (CpG-ODN) Adjuvant As Tumor Vaccines For Immunotherapy Of Cervical Cancer," Gynecologic Oncology 289(1):155-162.

Wei-Chiang, S. (2000). "Research Page: Arginine Deiminase as an Innovative Anti-Breast Cancer Agent," Initial Award Abstract (2pgs.), Research Priorities, Innovative Treatment Modalities New Drug Design: Creative Science, University of Southern California, 2 pages. (Abstract Only).

Wieneke, R. (Feb. 2019). "Selektive Proteinmarkierung Mit Nanometerpräzision in Lebenden Zellen," BIOspektrum 25(1):37-40.

(56) References Cited

OTHER PUBLICATIONS

Williams, A. R. et al. (Nov. 5, 1999). "Filtroporation: A simple, reliable technique for transfection and macromolecular loading of cells in suspension," Biotechnology And Bioengineering 65(3):341-346.

Wood, K.J. et al. (Jan. 1, 1985). "Antigen-Induced Suppression: The Role Of Class I Major Histocompatibility Antigens," Bioscience Reports 5(10-11):1007-1014.

Wright, A. et al. (Feb. 23, 2015). "Rational Design of a Split-Cas9 Enzyme Complex", PNAS 112(10):2984-2989.

Yang, Y.G. et al. (Nov. 4, 2015). "Carrier Erythrocytes And Its Application In Targeting Chemotherapy," Journal of Medical Postgraduates 17(11):1015-1018. (English Abstract Only).

Yarar, D. et al. (Feb. 2018). "A CellSqueeze®-Based Vaccine for Cancer Therapy," Poster, presented at the Keystone: Emerging Cellular Therapies—T Cells and Beyond Conference, Keystone, CO, Feb. 11-15, 2018, 1 page.

Yin, H. (Jun. 2017, e-pub. Mar. 24, 2017). "Delivery technologies for genome editing," Nature Reviews Drug Discovery 16(6):387-399.

You, Q. et al. (May 2, 2008). "Mechanism of T Cell Tolerance Induction by Murine Hepatic Kuoffer Cells," Hepatology 48(3):978-990.

Zarnitsyn, V. G. et al., "Electrosonic ejector microarray for drug and gene delivery" Biomed Microdevices (2008) 10:299-308.

Zdobnova, T. et al. (Oct. 25, 2012). "Self-Assembling Complexes of Quantum Dots and scFv Antibodies for Cancer Cell Targeting and Imaging", PLOS ONE 7(10):e48248, 8 pages.

Zocchi, E. et al. (Mar. 1989). "Encapsulation Of Doxorubicin In Liver-Targeted Erythrocytes Increases The Therapeutic Index Of The Drug In A Murine Metastatic Model," PNAS USA 86:2040-2044.

Howarth, M. et al. (May 2008). "Monovalent, Reduced-Size Quantum Dots For Imaging Receptors On Living Cells," Nature Methods 5(5):397-399, 7 pages.

International Preliminary Report on Patentability dated Sep. 15, 2020, for International Patent Application No. PCT/US2019/021705, filed Mar. 11, 2019, 14 pages.

International Preliminary Report on Patentability, dated Sep. 15, 2020, for Patent Application No. PCT/US2019/021703, filed Mar. 11, 2019, 10 pages.

International Search Report and Written Opinion, dated Sep. 14, 2020, for PCT Application No. PCT/US2020/026891, filed Apr. 6, 2020, 21 pages.

Kim, D. et al. (2009, e-pub. Apr. 13, 2009). "Microengineered Platforms for Cell Mechanobiology," Annual Review of Biomedical Engineering 11:203-233.

Liu, W. et al. (Jan. 20, 2010). "Compact Biocompatible Quantum Dots Via RAFT -Mediated Synthesis of Imidazole-Based Random Copolymer Ligand," JACS 132(2):472-483, 27 pages.

Matthews, B.D. et al. (2006). "Cellular Adaptation to Mechanical Stress: Role of Integrins, Rho, Cytoskeletal Tension And Mechanosensitive Ion Channels," Journal of Cell Science 119:508-518.

Murphy, J.S. et al. (Sep. 1, 1956, e-pub May 2004). "Measurement of Wall Shearing Stress in the Boundary Layer by Means of an Evaporating Liquid Film," Journal of Applied Physics 27(9):1097-1103, 9 pages.

\* cited by examiner

INTRACELLULAR DELIVERY OF BIOMOLECULES TO CELLS COMPRISING A CELL WALL

CROSS-REFERENCE TO RELATED APPLICATIONS

This application is a National Phase Filing under 35 U.S.C. 371 of International Application No. PCT/US2016/050288, having an International Filing Date of Sep. 2, 2016, which claims priority to U.S. Provisional Application No. 62/214,821, filed on Sep. 4, 2015 and U.S. Provisional Application No. 62/365,177, filed on Jul. 21, 2016, all of which are hereby incorporated by reference in their entireties.

FIELD OF THE INVENTION

The present disclosure relates generally to methods for delivering a compound into a cell comprising a cell wall by passing a cell suspension through a constriction.

BACKGROUND

Intracellular delivery is a central step in the research and development of engineered organisms. Existing technologies aimed at intracellular delivery of molecules rely on electrical fields, nanoparticles, or pore-forming chemicals. However, these methods suffer from numerous complications, including non-specific molecule delivery, modification or damage to the payload molecules, high cell death, low throughput, and/or difficult implementation. In addition, these intracellular delivery methods are not effective at delivering molecules to cells with cell walls, such as plant, yeast, fungal, algal, and prokaryotic cells. Thus, there is an unmet need for intracellular delivery techniques that are highly effective at delivering a range of molecules to a variety of cell types. In addition, techniques that allow for rapid, high throughput intracellular delivery can be applied more effectively to large scale clinical, manufacturing, and drug screening applications. References that describe methods of using channels to deliver compounds to cells include WO2013059343 and WO2015023982.

All references cited herein, including patent applications and publications, are incorporated by reference in their entirety.

BRIEF SUMMARY OF THE INVENTION

Certain aspects of the present disclosure include a method for delivering a compound into a cell comprising a cell wall, the method comprising passing a cell suspension through a constriction, wherein said constriction deforms the cell comprising a cell wall, thereby causing a perturbation of the cell such that the compound enters the cell, wherein said cell suspension is contacted with the compound.

Other aspects of the present disclosure include a method for delivering a compound into a cell modified to remove (such as digest or disrupt) all or part of a cell wall, the method comprising passing a cell suspension through a constriction, wherein said constriction deforms the cell modified to remove all or part of a cell wall, thereby causing a perturbation of the cell such that the compound enters the cell, wherein said cell suspension is contacted with the compound In some embodiments that can be combined with the previous embodiments, the constriction is contained within a microfluidic channel. In some embodiments, the constriction is a pore or contained within a pore. In some embodiments, the pore is contained in a surface. In some embodiments, the surface is a filter. In some embodiments, the surface is a membrane. In some embodiments, the constriction size is a function of the cell diameter. In some embodiments, the constriction size is about 20%, about 30%, about 40%, about 50%, about 60%, about 70%, about 80%, about 90%, or about 99% of the cell diameter.

In some embodiments that can be combined with the previous embodiments, the cell suspension comprises a mixed cell population. In some embodiments, the cell suspension comprises a purified cell population. In some embodiments, the cell comprising a cell wall is a plant, yeast, fungal, algal, or prokaryotic cell. In some embodiments, the plant cell is a crop, model, ornamental, vegetable, leguminous, conifer, or grass plant cell. In some embodiments, the yeast cell is a *Candida, Hansenula, Kluyveromyces, Pichia, Saccharomyces, Schizosaccharomyces,* or *Yarrowia* strain cell. In some embodiments, the fungal cell is an *Acremonium, Aspergillus, Fusarium, Humicola, Mucor, Myceliophthora, Neurospora, Penicillium, Scytalidium, Thielavia, Tolypocladium,* or *Trichoderma* strain cell. In some embodiments, the prokaryotic cell is a *Bacillus coagulans, Bacteroides fragilis, Bacteroides melaninogenicus, Bacteroides oralis, Bifidobacterium bifidum, Bifidobacterium breve, Bifidobacterium infantis, Bifidobacterium lactis, Bifidobacterium longum, Carboxydocella* sp., *Clostridium perfringens, Clostridium septicum, Clostridium tetani, Corynebacterium glutamicum, Enterobacteriaceae, Enterococcus faecalis, Erwinia chrysanthemi, Faecalibacterium prausnitzii, Lactobacillus acidophilus, Lactobacillus brevis, Lactobacillus bulgaricus, Lactobacillus fermentum, Lactobacillus gasseri, Lactobacillus paracasei, Lactobacillus plantarum, Lactobacillus reuteri, Lactobacillus rhamnosus, Lactobacillus salivarius, Lactobacillus* sp., *Pediococcus acidilactici, Peptococcus* sp., *Peptostreptococcus* sp., *Propionibacterium freudenreichii, Proteus mirabilis, Pseudomonas aeruginosa, Rhodopseudomonas capsulata, Salmonella enteritidis, Staphylococcus aureus, Streptococcus faecium, Streptococcus lactis, Streptococcus salivarius, Streptococcus thermophilus, Vibrio furnissii, Caldicellulosiruptor saccharolyticus, Xanthomonas campestris,* cyanobacteria, *Escherichia, Enterobacter, Azotobacter, Erwinia, Bacillus, Pseudomonas, Klebsiella, Proteus, Salmonella, Serratia, Shigella, Rhizobia, Vitreoscilla, Synechococcus, Synechocystis,* or *Paracoccus* cell. In some embodiments, the algal cell is a Chlorophyceae, Bacillariophyceae, Eustigmatophyceae, or Chrysophyceae cell.

In some embodiments that can be combined with the previous embodiments, the compound comprises a nucleic acid. In some embodiments, the compound comprises a nucleic acid encoding DNA, recombinant DNA, cDNA, genomic DNA, RNA, siRNA, mRNA, miRNA, lncRNA, tRNA, shRNA, or self-amplifying mRNA. In some embodiments, the compound comprises a peptide nucleic acid. In some embodiments, the compound comprises a transposon. In some embodiments, the compound is a plasmid. In some embodiments, the compound comprises a plastid. In some embodiments, the compound comprises a protein-nucleic acid complex. In some embodiments, the compound comprises a Cas9 protein and a guide RNA or donor DNA. In some embodiments, the compound comprises nucleic acid encoding for a Cas9 protein and a guide RNA or donor DNA. In some embodiments, the compound comprises a lipid-nucleic acid complex. In some embodiments, the compound comprises a cation-nucleic acid complex. In some embodiments, the compound comprises a protein or peptide. In some embodiments, the compound comprises a TALEN protein, Zinc finger nuclease, mega nuclease, CRE recombinase, FLP recombinase, R recombinase, integrase, or transposase. In some embodiments, the compound comprises a histone acetyltransferase, deacetylase, methyltransferase, or demethylase. In some embodiments, the compound is an antibody. In some embodiments, the compound is a transcription factor. In some embodiments, the compound is a small molecule. In some embodiments, the compound is a nanoparticle. In some embodiments, the compound is a liposome. In some embodiments, the compound is a fluorescently tagged molecule. In some embodiments, said cell suspension is contacted with the compound before, concurrently, or after passing through the constriction.

In some embodiments that can be combined with the previous embodiments, the cell is modified to remove all or part of the cell wall. In some embodiments, the cell suspension is treated with an enzyme to digest all or part of the cell wall prior to passing the cell suspension through the constriction. In some embodiments, the enzyme is one or more of cellulase, pectinase, xylanase, lysozyme, zymolyase, or chitinase. In some embodiments, the cell suspension is treated with heat or ultrasound to disrupt all or part of the cell wall prior to passing through the constriction.

DETAILED DESCRIPTION

Figure 1:
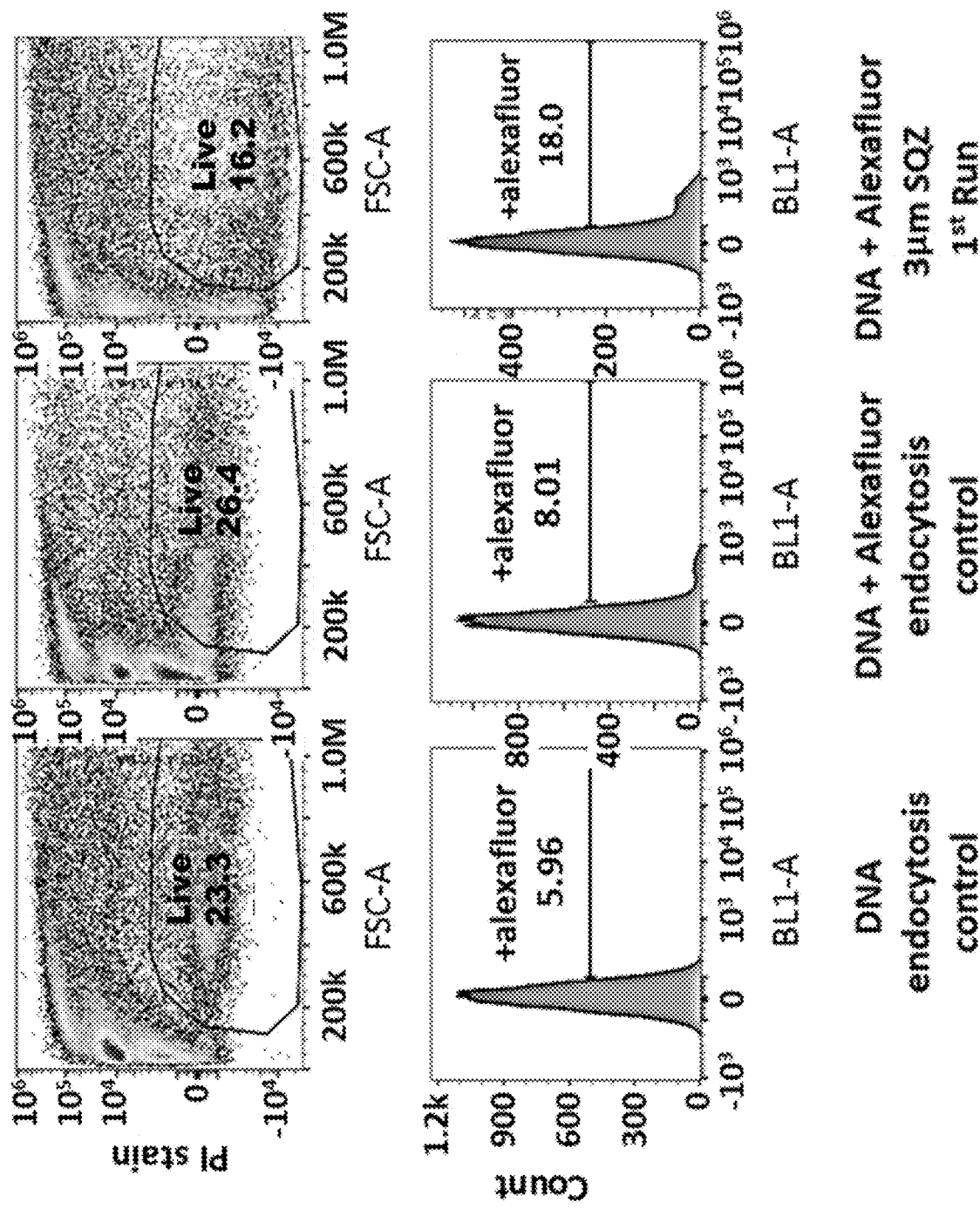
FIG. 1 shows the results of flow cytometry to identify live cells and cells incorporating a fluorescent dye following constriction-mediated delivery in S. cerevisiae cells.
Figure 1:
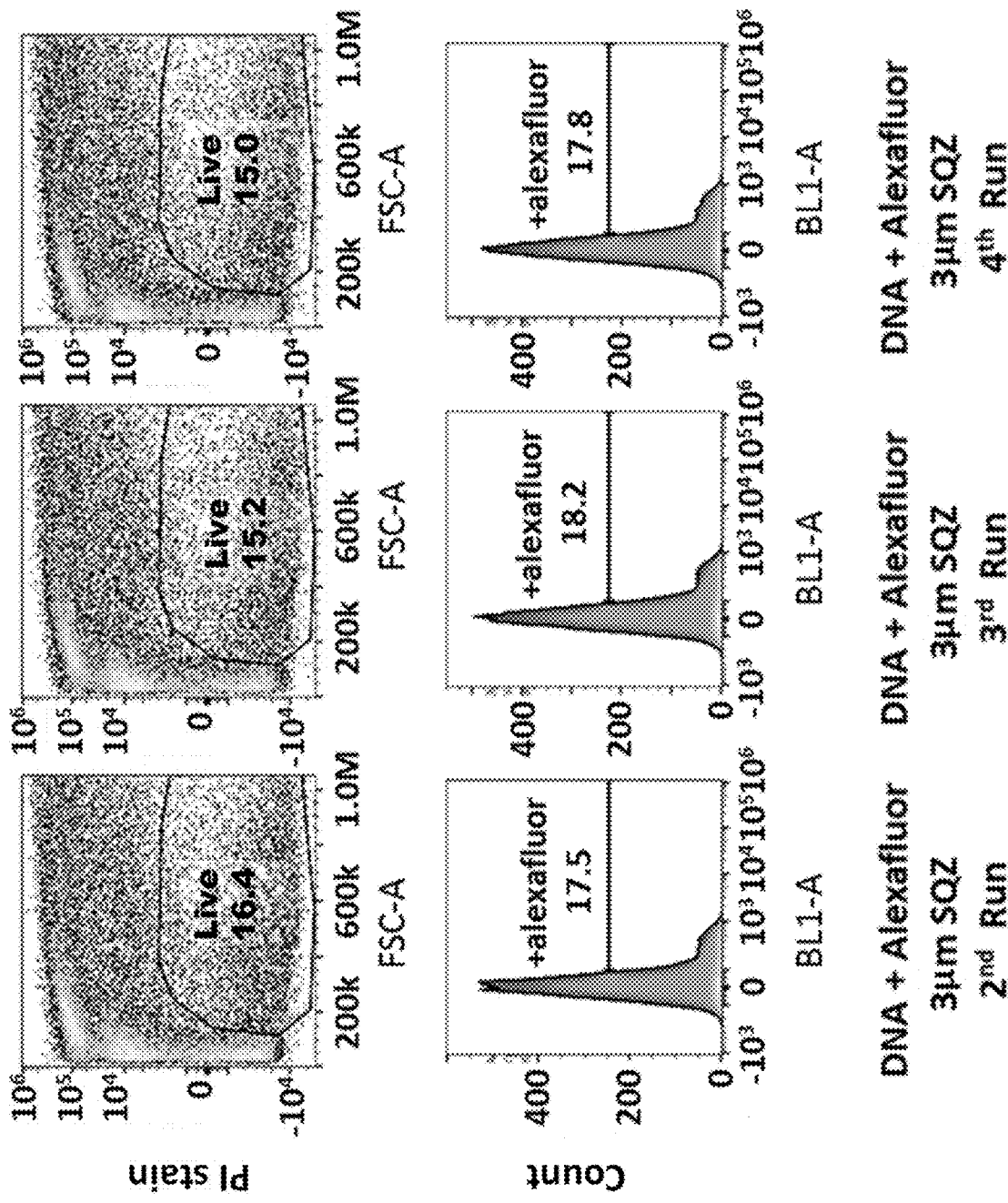

Certain aspects of the present disclosure relate to methods for delivering a compound into a cell comprising a cell wall or modified to remove all or part of a cell wall, the methods including passing a cell suspension through a constriction, wherein said constriction deforms the cell comprising a cell wall or modified to remove all or part of a cell wall, thereby causing a perturbation of the cell such that the compound enters the cell, wherein said cell suspension is contacted with the compound. In some embodiments, the constriction is contained within a microfluidic channel. In some embodiments, the constriction is a pore or contained within a pore. In some embodiments, the pore is contained in a surface. In some embodiments, the surface is a filter. In some embodiments, the surface is a membrane.

I. General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4$^{th}$ ed., Cold Spring Harbor Laboratory Press, Cold Spring Harbor, N.Y., 2012); *Current Protocols in Molecular Biology* (DOI: 10.1002/0471142727); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (E. A. Greenfield, eds., 2013); *Culture of Animal Cells: A Manual of Basic Technique and Specialized Applications* (R. I. Freshney, 6$^{th}$ ed., J. Wiley and Sons, 2010); *Oligonucleotides and Analogues* (F. Eckstein, ed., 1992); *Methods in Molecular Biology*, Humana Press; *Cell Biology: A Laboratory Handbook* (J. E. Celis, ed., Academic Press, 2005); *Introduction to Cell and Tissue Culture* (J. P. Mather and P. E. Roberts, Springer, 2013); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (DOI: 10.1002/0471142735); *Short Protocols in Molecular Biology* (Ausubel et al., eds., J. Wiley and Sons, 2002); *Janeway's Immunobiology* (K. Murphy and C. Weaver, Garland Science, 2016); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *Making and Using Antibodies: A Practical Handbook* (G. C. Howard and M. R. Kaser, eds., CRC Press, 2013); *The Antibodies* Vol. 1-7 (M. Zanetti and J. D. Capra, eds., Harwood Academic Publishers, 1995-2007); and *Cancer: Principles and Practice of Oncology* (V. T. DeVita et al., eds., J.B. Lippincott Company, 2011).

II. Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

It is understood that aspects and embodiments of the disclosure described herein include "comprising," "consisting," and "consisting essentially of" aspects and embodiments.

For all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the methods disclosed, but do not contain any other components which substantially affect the methods disclosed other than those components expressly listed; or, if the composition does contain extra components other than those listed which substantially affect the methods disclosed, the composition does not contain a sufficient concentration or amount of the extra components to substantially affect the methods disclosed. When a method is described as "consisting essentially of" the listed steps, the method contains the steps listed, and may contain other steps that do not substantially affect the methods disclosed, but the method does not contain any other steps which substantially affect the methods disclosed other than those steps expressly listed. As a non-limiting specific example, when a composition is described as 'consisting essentially of' a component, the composition may additionally contain any amount of pharmaceutically acceptable carriers, vehicles, or diluents and other such components which do not substantially affect the methods disclosed.

The term "about" as used herein refers to the usual error range for the respective value readily known to the skilled person in this technical field. Reference to "about" a value or parameter herein includes (and describes) embodiments that are directed to that value or parameter per se.

The term "cell wall" as used herein refers to an outer layer that surrounds certain cell types, such as plants, yeast, fungi, algae, and some prokaryotes. In some examples the term refers to a tough or rigid layer that surrounds the plasma membrane and provides support to the cell. In some examples, the cell wall may be composed of a number of materials, including without limitation, cellulose, hemicellulose, pectin, peptidoglycan, glucosamine, chitin, glycoproteins, or polysaccharides.

The term "constriction" as used herein refers to a narrowed passageway. In some examples, the constriction is contained within a microfluidic channel. In other examples, the constriction is a pore or contained within a pore. In some examples where the constriction is a pore, the pore is contained in a surface.

The term "pore" as used herein refers to an opening, including without limitation, a hole, tear, cavity, aperture, break, gap, or perforation within a material. In some examples, (where indicated) the term refers to a pore within a surface of the present disclosure. In other examples, (where indicated) a pore can refer to a pore in a cell wall and/or cell membrane.

The term "membrane" as used herein refers to a selective barrier or sheet containing pores. The term includes a pliable sheetlike structure that acts as a boundary or lining. In some examples, the term refers to a surface or filter containing pores. This term is distinct from the term "cell membrane".

The term "filter" as used herein refers to a porous article that allows selective passage through the pores. In some examples the term refers to a surface or membrane containing pores.

The term "heterogeneous" as used herein refers to something which is mixed or not uniform in structure or composition. In some examples the term refers to pores having varied sizes, shapes or distributions within a given surface.

The term "homogeneous" as used herein refers to something which is consistent or uniform in structure or composition throughout. In some examples the term refers to pores having consistent sizes, shapes, or distribution within a given surface.

The term "heterologous" as used herein refers to a molecule which is derived from a different organism. In some examples the term refers to a nucleic acid or protein which is not normally found or expressed within the given organism.

The term "homologous" as used herein refers to a molecule which is derived from the same organism. In some examples the term refers to a nucleic acid or protein which is normally found or expressed within the given organism.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—NH2) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

For any of the structural and functional characteristics described herein, methods of determining these characteristics are known in the art.

III. Cell Suspensions

In certain aspects, the present disclosure relates to passing a cell suspension through a constriction. In some embodiments, the cell suspension comprises a cell comprising a cell wall. In some embodiments, the cell suspension comprises a cell modified to remove all or part of a cell wall. In some embodiments, the cell comprising a cell wall or modified to remove all or part of a cell wall is a plant, yeast, fungal, algal, or prokaryotic cell. The cell suspension may be a mixed or purified population of cells. In some embodiments, the cell comprising a cell wall or modified to remove all or part of a cell wall is a eukaryotic cell.

In some embodiments, the cell comprising a cell wall or modified to remove all or part of a cell wall is a plant cell. In some embodiments, the plant cell is a crop, model, ornamental, vegetable, leguminous, conifer, or grass plant cell. Suitable plants include both monocotyledonous (monocot) plants and dicotyledonous (dicot) plants. In some embodiments, the plant cell is a plant cell line cell. In some embodiments, the plant cell is a recombinant plant cell. In some embodiments, the plant cell is a cultured plant cell.

Examples of crop plants, model plants, and vegetables include, without limitation, *Arabidopsis*, corn, rice, alfalfa, sunflower, canola, cotton, sorghum, wheat, tobacco, oat, barley, *lemna*, tomato, lettuce.

Examples of ornamental plants include, without limitation, azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbiapulcherrima*), and *chrysanthemum*.

Examples of leguminous plants include, without limitation, guar, locust bean, fenugreek, soybean, garden beans, cowpea, mungbean, green beans (*Phaseolus vulgaris*), peas (*Lathyrus* spp.), lima beans (*Phaseolus limensis*), fava bean, lentils, chickpea, peanuts (*Arachis* sp.), crown vetch (*Vicia* sp.), hairy vetch, adzuki bean, lupine (*Lupinus* sp.), *trifolium*, common bean (*Phaseolus* sp.), field bean (*Pisum* sp.), clover (*Melilotus* sp.), Lotus, trefoil, lens, and false indigo.

Examples of conifer plants include, without limitation, loblolly pine (*Pinus taeda*), slash pine (*Pinus elliotii*), ponderosa pine (*Pinus ponderosa*), lodgepole pine (*Pinus contorta*), Monterey pine (*Pinus radiata*), Douglas-fir (*Pseudotsuga menziesii*), Western hemlock (Isuga *canadensis*), Sitka spruce (*Picea glauca*), redwood (*Sequoia sempervirens*), silver fir (*Abies amabilis*), balsam fir (*Abies balsamea*), Western red cedar (*Thuja plicata*), and Alaska yellow-cedar (*Chamaecyparis nootkatensis*).

Examples of grass plants include, without limitation, alfalfa (*Medicago* sp.), orchard grass, tall fescue, perennial ryegrass, creeping bent grass, and redtop.

In some embodiments, the cell comprising a cell wall or modified to remove all or part of a cell wall is a yeast cell. In some embodiments, the yeast cell is a *Candida, Hansenula, Kluyveromyces, Pichia, Saccharomyces, Schizosaccharomyces,* or *Yarrowia* strain cell. "Yeast" as used herein includes ascosporogenous yeast (Endomycetales), basidiosporogenous yeast, and Fungi Imperfecti (Blastomycetes) yeast. In some embodiments, the yeast cell is a yeast cell line cell. In some embodiments, the yeast cell is a recombinant yeast cell. In some embodiments, the yeast cell is a cultured yeast cell.

In some embodiments, the yeast cell is a *Saccharomyces carlsbergensis, Saccharomyces cerevisiae, Saccharomyces diastaticus, Saccharomyces douglasii, Saccharomyces kluyveri, Saccharomyces norbensis, Saccharomyces monacensis, Saccharomyces bayanus, Saccharomyces pastorianus, Saccharomyces pombe,* or *Saccharomyces oviformis* strain cell. In some embodiments, the yeast cell is a *Kluyveromyces lactis, Kluyveromyces fragilis, Kluyveromyces marxiamus, Pichia stipitis, Candida shehatae,* or *Candida tropicalis* cell. In other embodiments, the yeast cell is a *Yarrowia lipolytica, Brettanomyces custersii,* or *Zygosaccharomyces roux* cell.

In some embodiments, the cell comprising a cell wall or modified to remove all or part of a cell wall is a fungal cell. In some embodiments, the fungal cell is an *Acremonium, Aspergillus, Fusarium, Humicola, Mucor, Myceliophthora, Neurospora, Penicillium, Scytalidium, Thielavia, Tolypocladium,* or *Trichoderma* strain cell. "Fungi" as used herein includes the phyla Ascomycota, Basidiomycota, Chytridiomycota, and Zygomycota as well as the Oomycota and all mitosporic fungi. In some embodiments, the fungal cell is a fungal cell line cell. In some embodiments, the fungal cell is a recombinant fungal cell. In some embodiments, the fungal cell is a cultured fungal cell.

In embodiments, the fungal cell is a filamentous fungal strain cell. "Filamentous fungi" include all filamentous forms of the subdivision Eumycota and Oomycota. In some embodiments, the filamentous fungal cell is an *Aspergillus awamori, Aspergillus foetidus, Aspergillus japonicus, Aspergillus nidulans, Aspergillus niger,* or *Aspergillus oryzae* strain cell. In other embodiments, the filamentous fungal cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* strain cell. In other embodiments, the filamentous fungal cell is a *Humicola insolens, Humicola lanuginosa, Mucor miehei, Myceliophthora thermophila, Neurospora crassa, Penicillium purpurogenum, Scytalidium thermophilum, Sporotrichum thermophile,* or *Thielavia terrestris* strain cell. In some embodiments, the filamentous fungal cell is a *Trichoderma harzianum, Trichoderma koningii, Trichoderma longibrachiatum, Trichoderma reesei,* or *Trichoderma viride* strain cell.

In some embodiments, the cell comprising a cell wall or modified to remove all or part of a cell wall is a prokaryotic cell. In some embodiments, the prokaryotic cell is a prokaryotic cell line cell. In some embodiments, the prokaryotic cell is a recombinant prokaryotic cell. In some embodiments, the prokaryotic cell is a cultured prokaryotic cell. In some embodiments, the prokaryotic cell is a gram-positive bacteria cell. Gram-positive bacteria have a cell wall comprising a thick peptidoglycan layer. In some embodiments, the prokaryotic cell is a gram-negative bacteria cell. Gram-negative bacterial have a cell wall comprising a thin peptidoglycan layer between an inner cytoplasmic cell membrane and an outer membrane. In some embodiments, the prokaryotic cell is a *Bacillus coagulans, Bacteroides fragilis, Bacteroides melaninogenicus, Bacteroides oralis, Bifidobacterium bifidum, Bifidobacterium breve, Bifidobacterium infantis, Bifidobacterium lactis, Bifidobacterium longum, Carboxydocella* sp., *Clostridium perfringens, Clostridium septicum, Clostridium tetani, Corynebacterium glutamicum,* Enterobacteriaceae, *Enterococcus faecalis, Erwinia chrysanthemi, Faecalibacterium prausnitzii, Lactobacillus acidophilus, Lactobacillus brevis, Lactobacillus bulgaricus, Lactobacillus fermentum, Lactobacillus gasseri, Lactobacillus paracasei, Lactobacillus plantarum, Lactobacillus reuteri, Lactobacillus rhamnosus, Lactobacillus salivarius, Lactobacillus* sp., *Pediococcus acidilactici, Peptococcus* sp., *Peptostreptococcus* sp., *Propionibacterium freudenreichii, Proteus mirabilis, Pseudomonas aeruginosa, Rhodopseudomonas capsulata, Salmonella enteritidis, Staphylococcus aureus, Streptococcus faecium, Streptococcus lactis, Streptococcus salivarius, Streptococcus thermophilus, Vibrio furnissii, Caldicellulosiruptor saccharolyticus, Xanthomonas campestris,* cyanobacteria, *Escherichia, Enterobacter, Azotobacter, Erwinia, Bacillus, Pseudomonas, Klebsiella, Proteus, Salmonella, Serratia, Shigella, Rhizobia, Vitreoscilla, Synechococcus, Synechocystis,* or *Paracoccus* cell. In some embodiments, the prokaryotic cell is an *E. coli, Bacillus subtilis, Zymomonas mobilis, Clostridium* sp., *Clostridium phytofermentans, Clostridium thermocellum, Clostridium beijerinckii, Clostridium acetobutylicum* (*Moorella thermoacetica*), *Thermoanaerobacterium saccharolyticum, Carboxydocella* sp., *Corynebacterium glutamicum,* Enterobacteriaceae, *Erwinia chrysanthemi, Lactobacillus* sp., *Pediococcus acidilactici, Rhodopseudomonas capsulata, Streptococcus lactis, Vibrio fumissii, Caldicellulosiruptor saccharolyticus,* or *Xanthomonas campestris* cell.

In some embodiments, the cell comprising a cell wall or modified to remove all or part of a cell wall is an algal cell. In some embodiments, the algal cell is a Chlorophyceae, Bacillariophyceae, Eustigmatophyceae, or Chrysophyceae cell. In some embodiments, the algal cell is an algal cell line cell. In some embodiments, the algal cell is a recombinant algal cell. In some embodiments, the algal cell is a cultured algal cell. In some embodiments, the algal cell is a *Chlamydomonas reinhardtii* cell. In some embodiments, the algal cell is a *Dunaliella* cell. In some embodiments, the algal cell is a *Chlorella* cell. In some embodiments, the algal cell is a *Spirulina* cell.

The composition of the cell suspension (e.g., osmolarity, salt concentration, ionic strength, protein content, cell concentration, pH, redox potential, etc.) can impact delivery of the compound. In some embodiments, the cell suspension comprises an aqueous solution. In some embodiments, the aqueous solution comprises cell culture medium, PBS, salts, sugars, growth factors, plant products, fungal products, yeast extract, bulking materials, surfactants, lubricants, vitamins, or proteins. Additionally, solution buffer can include one or more lubricants (pluronics or other surfactants) that can be designed to reduce or eliminate clogging of the constriction and improve cell viability.

IV. Microfluidic Channels

In certain aspects, the present disclosure relates to methods for delivering a compound into a cell comprising a cell wall or modified to remove all or part of a cell wall including the steps of passing a cell suspension through a constriction, wherein the constriction deforms the cell comprising a cell wall or modified to remove all or part of a cell wall, causing a perturbation of the cell, and contacting the cell suspension with the compound; e.g., before, during or after the cells in the suspension pass through the constriction. In some embodiments, the constriction is contained within a microfluidic channel. In some embodiments, multiple constrictions can be placed in parallel and/or in series within the microfluidic channel.

In some embodiments, the microfluidic channel includes a lumen and is configured such that a cell suspended in a buffer can pass through, wherein the microfluidic channel includes a constriction. The microfluidic channel can be made of any one of a number of materials, including silicon, metal (e.g., stainless steel), plastic (e.g., polystyrene), ceramics, glass, crystalline substrates, amorphous substrates, or polymers (e.g., Poly-methyl methacrylate (PMMA), PDMS, Cyclic Olefin Copolymer (COC), etc.). Fabrication of the microfluidic channel can be performed by any method known in the art, including dry etching, wet etching, photolithography, injection molding, laser ablation, or SU-8 masks.

In some embodiments, the constriction within the microfluidic channel includes an entrance portion, a centerpoint, and an exit portion. In some embodiments, the length, depth, and width of the constriction within the microfluidic channel can vary. In some embodiments, the diameter of the constriction within the microfluidic channel is a function of the diameter of the cell comprising a cell wall or modified to remove all or part of a cell wall. In some embodiments, the diameter of the constriction within the microfluidic channel is about 20% to about 99% of the diameter of the cell. In some embodiments, the constriction size is about 20%, about 30%, about 40%, about 50%, about 60%, about 70%, about 80%, about 90%, or about 99% of the cell diameter. The cross-section of the channel, the entrance portion, the centerpoint, and the exit portion can also vary. For example, the cross-sections can be circular, elliptical, an elongated slit, square, hexagonal, or triangular in shape. The entrance portion defines a constriction angle, wherein the constriction angle is optimized to reduce clogging of the channel. The angle of the exit portion can vary as well. For example, the angle of the exit portion is configured to reduce the likelihood of turbulence that can result in non-laminar flow. In some embodiments, the walls of the entrance portion and/or the exit portion are linear. In other embodiments, the walls of the entrance portion and/or the exit portion are curved.

In some embodiments, the cross-sectional area of the pore is a function of the cross-sectional area of the cell. In some embodiments, the two-dimensional shape of the pore is circular, elliptical, square, rectangular, star-shaped, triangular, polygonal, pentagonal, hexagonal, heptagonal, or octagonal and the cross-sectional area of the pore is a function of the cross-sectional area of the cell. In some embodiments, the pore cross-sectional area is at least about 1 $\mu m^2$, 4 $\mu m^2$, 9 $\mu m^2$, 16 $\mu m^2$, 25 $\mu m^2$, 50 $\mu m^2$, 100 $\mu m^2$, 150 $\mu m^2$, 200 $\mu m^2$, 250 $\mu m^2$ 500 $\mu m^2$ or 1000 $\mu m^2$. In some embodiments, the pores are heterogeneous in cross-sectional area or homogeneous in cross-sectional area across a given surface. In some embodiments, the heterogeneous pore cross-sectional area varies from 10-20% or any percentage or range of percentages therebetween. In some embodiments, the pore deforms the cell to about any one of about 5%, 10%, 20%, 30%, 40%, 50%, 60%, 70%, 80%, 90% or 99% of the cross-sectional area of the cell or any value therebetween. In some embodiments, the size of the cell is the size of the cell in suspension.

V. Surface Having Pores

In certain aspects, the present disclosure relates to methods for delivering a compound into a cell comprising a cell wall or modified to remove all or part of a cell wall comprising the steps of passing a cell suspension through a constriction, wherein the constriction deforms the cell comprising a cell wall or modified to remove all or part of a cell wall, causing a perturbation of the cell, and contacting the cell suspension with the compound; e.g., before, during or after the cells in the suspension pass through the constriction, wherein the compound enters the cell. In some embodiments, the constriction is a pore or contained within a pore. In some embodiments, the pore is contained in a surface.

The surfaces as disclosed herein can be made of any one of a number of materials and take any one of a number of forms. In some embodiments, the surface is a filter. In some embodiments, the surface is a membrane. In some embodiments, the filter is a tangential flow filter. In some embodiments, the surface is a sponge or sponge-like matrix. In some embodiments, the surface is a matrix.

In some embodiments the surface is a tortuous path surface. In some embodiments, the tortuous path surface comprises cellulose acetate. In some embodiments, the surface comprises a material selected from, without limitation, synthetic or natural polymers, polycarbonate, silicon, glass, metal, alloy, cellulose nitrate, silver, cellulose acetate, nylon, polyester, polyethersulfone, Polyacrylonitrile (PAN), polypropylene, PVDF, polytetrafluorethylene, mixed cellulose ester, porcelain, and ceramic.

The surface disclosed herein can have any shape known in the art; e.g. a 3-dimensional shape. The 2-dimensional shape of the surface can be, without limitation, circular, elliptical, round, square, star-shaped, triangular, polygonal, pentagonal, hexagonal, heptagonal, or octagonal. In some embodiments, the surface is round in shape. In some embodiments, the surface 3-dimensional shape is cylindrical, conical, or cuboidal.

The surface can have various cross-sectional widths and thicknesses. In some embodiments, the surface cross-sectional width is between about 1 mm and about 1 m or any cross-sectional width or range of cross-sectional widths therebetween. In some embodiments, the surface has a defined thickness. In some embodiments, the surface thickness is uniform. In some embodiments, the surface thickness is variable. For example, in some embodiments, portions of the surface are thicker or thinner than other portions of the surface. In some embodiments, the surface thickness varies by about 1% to about 90% or any percentage or range of percentages therebetween. In some embodiments, the surface is between about 0.01 µm to about 0.02 µm, about 0.02 µm to about 0.03 µm, about 0.03 µm to about 0.04 µm, about 0.04 µm to about 0.05 µm, about 0.05 µm to about 0.06 µm, about 0.06 µm to about 0.07 µm, about 0.07 µm to about 0.08 µm, about 0.08 µm to about 0.09 µm, about 0.09 µm to about 0.1 µm, about 0 µm to about 0.2 µm, about 0.2 µm to about 0.3 µm, about 0.3 µm to about 0.4 µm, about 0.4 µm to about 0.5 µm, about 0.5 µm to about 0.6 µm, about 0.6 µm to about 0.7 µm, about 0.7 µm to about 0.8 µm, about 0.8 µm to about 0.9 µm, about 0.9 µm to about 1 µm, about 1 µm to about 2 µm, about 2 µm to about 3 µm, about 3 µm to about 4 µm, about 4 µm to about 5 µm, about 5 µm to about 6 µm, about 6 µm to about 7 µm, about 7 µm to about 8 µm, about 8 µm to about 9 µm, about 9 µm to about 10 µm, about 10 µm to about 20 µm, about 20 µm to about 30 µm, about 30 µm to about 40 µm, about 40 µm to about 50 µm, about 50 µm to about 60 µm, about 60 µm to about 70 µm, about 70 µm to about 80 µm, about 80 µm to about 90 µm, about 90 µm to about 100 µm, about 100 µm to about 200 µm, about 200 µm to about 300 µm, about 300 µm to about 400 µm, about 400 µm to about 500 µm, about 500 µm to about 600 µm, about 600 µm to about 700 µm, about 700 µm to about 800 µm, about 800 µm to about 900 µm, about 900 µm to about 1 mm, about 1 mm to about 2 mm, about 2 mm to about 3 mm, about 3 mm to about 4 mm, about 4 mm to about 5 mm thick or any thickness or range of thicknesses therebetween. In some embodiments, the surface is between about 0.01 µm to about 5 mm thick or any thickness or range of thicknesses therebetween.

In some embodiments, the constriction is a pore or contained within a pore. The cross-sectional width of the pores is related to the type of cell to be treated. In some embodiments, the pore size is a function of the diameter of the cell to be treated. In some embodiments, the pore size is such that a cell is perturbed upon passing through the pore. In some embodiments, the pore size is less than the diameter of the cell. In some embodiments, the pore size is about 20% to about 99% of the diameter of the cell. In some embodiments, the pore size is about 20%, about 30%, about 40%, about 50%, about 60%, about 70%, about 80%, about 90%, or about 99% of the cell diameter. Optimal pore size can vary based upon the application and/or cell type.

The entrances and exits of the pore passage may have a variety of angles. The pore angle can be selected to minimize clogging of the pore while cells are passing through. In some embodiments, the flow rate through the surface is between about 0.001 mL/cm$^2$/sec to about 100 L/cm$^2$/sec or any rate or range of rates therebetween. For example, the angle of the entrance or exit portion can be between about 0 and about 90 degrees. In some embodiments, the pores have identical entrance and exit angles. In some embodiments, the pores have different entrance and exit angles. In some embodiments, the pore edge is smooth, e.g. rounded or curved. A smooth pore edge has a continuous, flat, and even surface without bumps, ridges, or uneven parts. In some embodiments, the pore edge is sharp. A sharp pore edge has a thin edge that is pointed or at an acute angle. In some embodiments, the pore passage is straight. A straight pore passage does not contain curves, bends, angles, or other irregularities. In some embodiments, the pore passage is curved. A curved pore passage is bent or deviates from a straight line. In some embodiments, the pore passage has multiple curves, e.g. about 2, 3, 4, 5, 6, 7, 8, 9, 10 or more curves.

The pores can have any shape known in the art, including a 2-dimensional or 3-dimensional shape. The pore shape (e.g., the cross-sectional shape) can be, without limitation, circular, elliptical, round, square, star-shaped, triangular, polygonal, pentagonal, hexagonal, heptagonal, and octagonal. In some embodiments, the cross-section of the pore is round in shape. In some embodiments, the 3-dimensional shape of the pore is cylindrical or conical. In some embodiments, the pore has a fluted entrance and exit shape. In some embodiments, the pore shape is homogenous (i.e. consistent or regular) among pores within a given surface. In some embodiments, the pore shape is heterogeneous (i.e. mixed or varied) among pores within a given surface.

The terms "pore size" and "pore cross-sectional width" are used interchangeably, and as used herein refer to the smallest cross-sectional width across the pore. In some embodiments, the pore is circular or roughly circular and the pore size or pore cross sectional width. In some embodiments, the pore is polygonal in shape (e.g., square, rectangular, pentagonal, hexagonal, etc.) and the pore size or pore cross sectional width is the smallest width of the polygon. One skilled in the art would understand that a triangular pore may not have a width, but rather, is described in terms of bases and heights. In some embodiments, the pore size or pore cross sectional width of a triangular pore is the smallest height of the triangle (smallest distance between a base and its opposite angle).

The surfaces described herein can have a range of total pore numbers. In some embodiments, the pores encompass about 10% to about 80% of the total surface area. In some embodiments, the surface contains about $1.0 \times 10^5$ to about $1.0 \times 10^{30}$ total pores or any number or range of numbers therebetween. In some embodiments, the surface comprises between about 10 and about $1.0 \times 10^{15}$ pores per mm$^2$ surface area.

The pores can be distributed in numerous ways within a given surface. In some embodiments, the pores are distributed in parallel within a given surface. In one such example, the pores are distributed side-by-side in the same direction and are the same distance apart within a given surface. In some embodiments, the pore distribution is ordered or homogeneous. In one such example, the pores are distributed in a regular, systematic pattern or are the same distance apart within a given surface. In some embodiments, the pore distribution is random or heterogeneous. In one such example, the pores are distributed in an irregular, disordered pattern or are different distances apart within a given surface. In some embodiments, multiple surfaces are distributed in series. The multiple surfaces can be homogeneous or heterogeneous in surface size, shape, and/or roughness. The multiple surfaces can further contain pores with homogeneous or heterogeneous pore size, shape, and/or number, thereby enabling the simultaneous delivery of a range of compounds into different cell types.

In some embodiments, an individual pore has a uniform width dimension (i.e. constant width along the length of the pore passage). In some embodiments, an individual pore has a variable width (i.e. increasing or decreasing width along the length of the pore passage). In some embodiments, pores within a given surface have the same individual pore depths. In some embodiments, pores within a given surface have different individual pore depths. In some embodiments, the pores are immediately adjacent to each other. In some embodiments, the pores are separated from each other by a distance. In some embodiments, the pores are separated from each other by a distance of about 0.001 μm to about 30 mm or any distance or range of distances therebetween.

In some embodiments, the surface is coated with a material. The material can be selected from any material known in the art, including, without limitation, Teflon, an adhesive coating, surfactants, proteins, adhesion molecules, antibodies, anticoagulants, factors that modulate cellular function, nucleic acids, lipids, carbohydrates, or transmembrane proteins. In some embodiments, the surface is coated with polyvinylpyrrolidone. In some embodiments, the material is covalently attached to the surface. In some embodiments, the material is non-covalently attached to the surface. In some embodiments, the surface molecules are released at the cells pass through the pores.

In some embodiments, the surface has modified chemical properties. In some embodiments, the surface is hydrophilic. In some embodiments, the surface is hydrophobic. In some embodiments, the surface is charged. In some embodiments, the surface is positively and/or negatively charged. In some embodiments, the surface can be positively charged in some regions and negatively charged in other regions. In some embodiments, the surface has an overall positive or overall negative charge. In some embodiments, the surface can be any one of smooth, electropolished, rough, or plasma treated. In some embodiments, the surface comprises a zwitterion or dipolar compound.

In some embodiments, the surface is contained within a larger module. In some embodiments, the surface is contained within a syringe, such as a plastic or glass syringe. In some embodiments, the surface is contained within a plastic filter holder. In some embodiments, the surface is contained within a pipette tip.

VI. Compounds to Deliver

In certain aspects, the present disclosure relates to methods for delivering a compound into a cell comprising a cell wall or modified to remove all or part of a cell wall. In some embodiments, the compound is a single compound. In some embodiments, the compound is a mixture of compounds. In some embodiments, a compound or mixture of compounds is delivered to a cell comprising a cell wall or modified to remove all or part of a cell wall to produce a desired effect.

In some embodiments, the compound comprises a nucleic acid. In some embodiments, the compound is a nucleic acid. Exemplary nucleic acids include, without limitation, recombinant nucleic acids, DNA, recombinant DNA, cDNA, genomic DNA, RNA, siRNA, mRNA, saRNA, miRNA, lncRNA, tRNA, shRNA, self-amplifying mRNA, and peptide nucleic acids. In some embodiments, the nucleic acid is homologous to a nucleic acid in the cell. In some embodiments, the nucleic acid is heterologous to a nucleic acid in the cell. In some embodiments, the nucleic acid comprises a transposon, and optionally a sequence encoding a transposase. In some embodiments, the compound is a plasmid. In some embodiments, the nucleic acid is a therapeutic nucleic acid. In some embodiments, the nucleic acid encodes a therapeutic polypeptide. In some embodiments the nucleic acid encodes a reporter or a selectable marker. Exemplary reporter markers include, without limitation, green fluorescent protein (GFP), red fluorescent protein (RFP), auquorin, beta-galactosidase, Uroporphyrinogen (urogen) III methyltransferase (UMT), and luciferase. Exemplary selectable markers include, without limitation, Blasticidin, G418/GENETICIN™ (gentamicin), Hygromycin B, Puromycin, ZEOCIN® (phleomycin), nourseothricin (NTC), Adenine Phosphoribosyltransferase, and thymidine kinase. In some embodiments, the nucleic acid encodes a growth factor or inducer.

In some embodiments, the compound comprises an organelle comprising a nucleic acid. In some embodiments, the compound is an organelle comprising a nucleic acid. In some embodiments, the organelle is a double-membrane organelle, such as a plastid. In some embodiments, the organelle is a plant organelle, such as a plant plastid. In some embodiments, the plant organelle is a plastid that can include, without limitation, chloroplasts, chromoplasts, gerontoplasts, leucoplasts, amyloplasts, elaioplasts, proteinoplasts, and tannosomes. In some embodiments, the organelle is an algal organelle, such as an algal plastid. In some embodiments, the algal organelle is a plastid that can include, without limitation, leucoplasts, muroplasts, and rhodoplasts.

In some embodiments, the compound comprises a protein-nucleic acid complex. In some embodiments, the compound is a protein-nucleic acid complex. In some embodiments, protein-nucleic acid complexes, such as clustered regularly interspaced short palindromic repeats (CRISPR)-Cas9, are used in genome editing applications. These complexes contain sequence-specific DNA-binding domains in combination with nonspecific DNA cleavage nucleases. These complexes enable targeted genome editing, including adding, disrupting, or changing the sequence of a specific gene. In some embodiments, a disabled CRISPR is used to block or induce transcription of a target gene. In some embodiments, the compound contains a Cas9 protein and a guide RNA or donor DNA. In some embodiments, the compound includes a nucleic acid encoding for a Cas9 protein and a guide RNA or donor DNA. In some embodiments, the compound includes a transposase protein and a nucleic acid comprising a transposon.

In some embodiments, the compound comprises a lipid-nucleic acid complex. In some embodiments, the compound is a lipid-nucleic acid complex. In some embodiments, lipid-nucleic acid complexes are used to increase efficiency of delivering the nucleic acid into the cell. Exemplary nucleic acids include any of the nucleic acids described herein. In some embodiments, the lipid-nucleic acid complex comprises a cationic lipid and optionally a neutral helper lipid. In some embodiments, the cationic lipid can include, without limitation, N-[1-(2,3-dioleyloxy)propyl]-N,N,N-trimethylammonium chloride (DOTMA), [1,2-bis(oleoyloxy)-3-(trimethylammonio)propane] (DOTAP), 3β[N—(N',N'-dimethylaminoethane)-carbamoyl]cholesterol (DC-Chol), dioctadecylamidoglycylspermine (DOGS), and 2,3-dioleyloxy-N-[2(sperminecarboxamido)ethyl]-N,N-dimethyl-1-propanaminium trifluoroacetate (DOSPA). In some embodiments, the neutral helper lipid can include, without limitation, dioleoylphosphatidylethanolamine (DOPE) and dioleoylphosphatidylcholine (DOPC). In some embodiments, a lipid in the lipid-nucleic acid complex is modified with a polymer, such as polyethylene glycol (PEG).

In some embodiments, the compound comprises a cation-nucleic acid complex. In some embodiments, the compound is a cation-nucleic acid complex. In some embodiments, cation-nucleic acid complexes are used to increase efficiency of delivering the nucleic acid into the cell. Exemplary nucleic acids include any of the nucleic acids described herein. In some embodiments, the cation is a polycation. In some embodiments, the cation-nucleic acid complex comprises a cation that can include, without limitation, lithium, cesium, calcium, and polylysine (PLL).

In some embodiments, the compound comprises a protein or polypeptide. In some embodiments, the compound is a protein or polypeptide. In some embodiments, the protein or polypeptide is a therapeutic protein, antibody, growth factor or inducer, fusion protein, antigen, synthetic protein, reporter marker, or selectable marker. In some embodiments, the protein is a gene-editing protein such as a zinc-finger nuclease (ZFN), transcription activator-like effector nuclease (TALEN), mega nuclease, CRE recombinase, FLP recombinase, R recombinase, integrase, or transposase. In some embodiments, the fusion proteins can include, without limitation, chimeric protein drugs such as antibody drug conjugates or recombinant fusion proteins such as proteins tagged with GST or streptavidin. In some embodiments, the compound is a transcription factor. In some embodiments, the compound is chromatin remodeling protein that can include, without limitation, histone acetyltransferases (HATs), deacetylases, methyltransferases, demethylases, and kinases. HATs can include, without limitation, Gcn5, PCAF, Hat1, Elp3, Hpa2, Hpa3, ATF-2, Nut1, MOZ, Ybf2 (Sas3), Sas2, Tip60, Esa1, MOF, MORF, HBO1, p300, CBP, SRC-1, SRC-3, ACTR, TIF-2, $TAF_{II}250$, TFIIIC, Rtt109, and CLOCK. Deactylases can include, without limitation, HDAC1, HDAC2, HDAC3, HDAC4, HDAC5, HDAC6, HDAC7, HDAC8, HDAC9, HDAC10, HDAC11, SIRT1, SIRT2, SIRT3, SIRT4, SIRT5, SIRT6, SIRT7, SIRT8, and Sir2. Methyltransferases can include, without limitation, ASH1L, DOT1L, EHMT1, EHMT2, EZH1, EZH2, MLL, MLL2, MLL3, MLL4, MLL5, NSD1, PRDM2, SET, SETBP1, SETD1A, SETD1B, SETD2, SETD3, SETD4, SETD5, SETD6, SETD7, SETD8, SETD9, SETDB1, SETDB2, SETMAR, SMYD1, SMYD2, SMYD3, SMYD4, SMYD5, SUV39H1, SUV39H2, SUV420H1, and SUV420H2. Demethylases can include, without limitation, KDM1A, KDM1B, KDM2A, KDM2B, KDM3A, KDM3B, JMJD1C, KDM4A, KDM4B, KDM4C, KDM4D, KDM5A, KDM5B, KDM5C, KDM5D, KDM6A, KDM6B, and UTY.

In some embodiments the protein or polypeptide is a reporter or a selectable marker. Exemplary reporter markers include, without limitation, green fluorescent protein (GFP), red fluorescent protein (RFP), auquorin, beta-galactosidase, Uroporphyrinogen (urogen) III methyltransferase (UMT), and luciferase. Exemplary selectable markers include, without limitation, Blasticidin, G418/GENETICIN™ (gentamicin), Hygromycin B, Puromycin, ZEOCIN® (phleomycin), Adenine Phosphoribosyltransferase, and thymidine kinase.

In some embodiments, the compound comprises an antibody. In some embodiments, the compound is an antibody. In some embodiments, the antibody is a full length antibody or an antibody fragment. Antibodies for use in the present disclosure include, without limitation, antibody variants, labeled antibodies, antibody fragments such as Fab or $F(ab)_2$ fragments, single-domain antibodies, single-chain antibodies, multi-specific antibodies, antibody fusion proteins, and immunoadhesins. The antibodies may be any isotype known in the art, including IgA, IgG, IgE, IgD, or IgM.

In some embodiments, the compound comprises a small molecule. In some embodiments, the compound is a small molecule. Exemplary small molecules include, without limitation, fluorescent markers, dyes, pharmaceutical agents, metabolites, or radionucleotides. In some embodiments, the pharmaceutical agent is a therapeutic drug and/or cytotoxic agent.

In some embodiments, the compound comprises a nanoparticle. Examples of nanoparticles include gold nanoparticles, quantum dots, carbon nanotubes, nanoshells, dendrimers, and liposomes. In some embodiments, the nanoparticle contains a therapeutic molecule. In some embodiments, the nanoparticle contains a nucleic acid, such as mRNA. In some embodiments, the nanoparticle contains a label, such as a fluorescent or radioactive label.

In some embodiments, the compound comprises a fluorescently tagged molecule. In some embodiments, the compound is a fluorescently tagged molecule, such as a molecule tagged with a fluorochrome such as pacific blue, Alexa 288, Cy5, or cascade blue. In some embodiments, the compound is a radionucleotide, dextran particle, magnetic bead, or impermeable dye. In some embodiments, the compound is a 3 kDa dextran particle labeled with PacBlue. In some embodiments, the compound is a 10 kDa dextran particles labeled with Alexa488. In some embodiments, the compound is a small molecule fluorophore tagged protein. In some embodiments, the compound is a small molecule tagged with Alexa647.

In some embodiments, the compound to deliver is purified. In some embodiments, the compound is at least about 20% by weight (dry weight) the compound of interest. In some embodiments, the purified compound is at least about 30%, 40%, 50%, 60%, 70%, 80%, 90%, or 99% the compound of interest. In some embodiments, the purified compound is at least about 90%, 91%, 92%, 93%, 94%, 95%, 98%, 99%, or 100% (w/w) the compound of interest. Purity is determined by any known methods, including, without limitation, column chromatography, thin layer chromatography, HPLC analysis, NMR, mass spectrometry, or SDS-PAGE. Purified DNA or RNA is defined as DNA or RNA that is free of exogenous nucleic acids, carbohydrates, and lipids.

VII. Cell Perturbations

In certain aspects, the present disclosure relates to passing a cell suspension through a constriction, wherein the constriction deforms the cell comprising a cell wall or modified to remove (such as digest or disrupt) all or part of a cell wall, causing a perturbation of the cell. In some embodiments, the perturbation is a perturbation in the cell wall. In some embodiments, the perturbation is a perturbation in the cell membrane. In some embodiments, the perturbation is a perturbation in both the cell wall and the cell membrane. In some embodiments, the cell wall is treated prior to passing through the constriction to alter the cell wall. In some embodiments, the cell wall is treated using chemicals, enzymes such as cellulase, pectinase, xylanase, lysozyme, zymolyase, or chitinase, heat, or ultrasound prior to passing through the constriction. In some embodiments, treating a cell with an enzyme such as cellulase, pectinase, xylanase, lysozyme, zymolyase, or chitinase results in digestion of all or part of the cell wall. In some embodiments, treating a cell with heat or ultrasound results in disruption of all or part of the cell wall. In some embodiments, the cell wall is treated more than about any of 1 minute, 5 minutes, 10 minutes, 15 minutes, 20 minutes, 25 minutes, 30 minutes, 45 minutes, 1 hour, 2 hours, 4 hours, 6 hours, 12 hours, 24 hours or any time therebetween prior to passing the cell through the constriction. In some embodiments, disruption of the well is disruption of more than about 5%, 10%, 20%, 30%, 40%, 50%, 60%, 70%, 80%, 90%, 95%, or 99% of the cell wall. Methods to measure cell wall disruption are known in the art; for example, confocal microscopy, electron microscopy, atomic force microscopy (Dupre), and time-of-flight secondary ion mass spectrometry (ToF-SIMS). In some embodiments, the cell wall is not treated prior to passing through the constriction. The deformation in the cell can be caused by, for example, pressure induced by mechanical strain and/or shear forces. The perturbation in the cell is a breach in the cell that allows material from outside the cell to move into the cell (e.g., a hole, tear, cavity, aperture, pore, break, gap, perforation). In some embodiments, the perturbation is transient. In some embodiments, as the cell passes through the constriction, the deformation temporarily imparts injury to the cell wall that causes passive diffusion of material through the perturbation. In some embodiments, the constriction deforms the cell to about any one of about 5%, 10%, 20%, 30%, 40%, 50%, 60%, 70%, 80%, 90% or 99% of the diameter of the cell or any value therebetween. In some embodiments, the passage of the compound into the cell occurs simultaneously with the cell passing through the constriction and/or the perturbation of the cell. In some embodiments, passage of the compound into the cell occurs after the cell passes through the constriction.

VIII. Delivery Parameters

In certain aspects, the present disclosure relates to methods for delivering a compound into a cell comprising a cell wall including the steps of passing a cell suspension through a constriction, wherein the constriction deforms the cell comprising a cell wall, causing a perturbation of the cell, and contacting the cell suspension with the compound. In other aspects, the present disclosure relates to methods for delivering a compound into a cell modified to remove all or part of a cell wall including the steps of passing a cell suspension through a constriction, wherein the constriction deforms the cell modified to remove all or part of a cell wall, causing a perturbation of the cell, and contacting the cell suspension with the compound. The cell suspension may be contacted with the compound before, concurrently, or after passing through the constriction. The cell comprising a cell wall or modified to remove all or part of a cell wall may pass through the constriction suspended in a solution that includes the compound to deliver, although the compound can be added to the cell suspension after the cells pass through the constriction. In some embodiments, the compound to be delivered is coated on the constriction.

Several parameters can influence the delivery of the compound into the cell comprising a cell wall or modified to remove all or part of a cell wall. For example, the dimensions of the constriction, the entrance angle of the constriction, the surface properties of the constrictions (e.g. roughness, chemical modification, hydrophilic, hydrophobic, etc.), the operating flow speeds (e.g., cell transit time to the constriction), the cell concentration, the concentration of the compound in the cell suspension, and the amount of time that the cell recovers or incubates after passing through the constrictions can affect the passage of the delivered compound into the cell. Additional parameters influencing the delivery of the compound into the cell can include the velocity of the cell in the constriction, the shear rate in the constriction, the viscosity of the cell suspension, the velocity component that is perpendicular to flow velocity, and time in the constriction. Such parameters can be designed to control delivery of the compound. In some embodiments, the cell concentration ranges from about 10 to about $10^{20}$ cells/ml or any concentration or range of concentrations therebetween. In some embodiments, the cell concentration ranges from about 10 to about $10^2$, $10^2$ to about $10^3$, $10^3$ to about $10^4$, $10^4$ to about $10^5$, $10^5$ to about $10^6$, $10^6$ to about $10^7$, $10^7$ to about $10^8$, $10^8$ to about $10^9$, $10^9$ to about $10^{10}$, $10^{10}$ to about $10^{11}$, $10^{11}$ to about $10^{12}$, $10^{12}$ to about $10^{13}$, $10^{13}$ to about $10^{14}$, $10^{14}$ to about $10^{15}$, $10^{15}$ to about $10^{16}$, $10^{16}$ to about $10^{17}$, $10^{17}$ to about $10^{18}$, $10^{18}$ to about $10^{19}$, $10^{19}$ to about $10^{20}$, or any concentration or range of concentrations therebetween. In some embodiments, delivery compound concentrations can range from about 10 ng/ml to about 1 g/mL or any concentration or range of concentrations therebetween. In some embodiments, delivery compound concentrations can range from about 1 pM to about 2M or any concentration or range of concentrations therebetween.

The temperature used in the methods of the present disclosure can be adjusted to affect compound delivery and cell viability. In some embodiments, the method is performed between about −5° C. and about 45° C. For example, the methods can be carried out at room temperature (e.g., about 20° C.), physiological temperature (e.g., about 37° C.), higher than physiological temperature (e.g., greater than about 37° C. to 45° C. or more), or reduced temperature (e.g., about −5° C. to about 4° C.), or temperatures between these exemplary temperatures.

Various methods can be utilized to drive the cells comprising a cell wall through the constrictions. For example, pressure can be applied by a pump on the entrance side (e.g., gas cylinder, or compressor), a vacuum can be applied by a vacuum pump on the exit side, capillary action can be applied through a tube, and/or the system can be gravity fed. Displacement based flow systems can also be used (e.g., syringe pump, peristaltic pump, manual syringe or pipette, pistons, etc.). In some embodiments, the cells are passed through the constrictions by positive pressure or negative pressure. In some embodiments, the cells are passed through the constrictions by constant pressure or variable pressure. In some embodiments, pressure is applied using a syringe. In some embodiments, pressure is applied using a pump. In some embodiments, the pump is a peristaltic pump. In some embodiments, pressure is applied using a vacuum. In some embodiments, the cells are passed through the constrictions by g-force. In some embodiments, the cells are passed through the constrictions by capillary pressure.

In some embodiments, fluid flow directs the cells through the constrictions. In some embodiments, the fluid flow is turbulent flow prior to the cells passing through the constriction. Turbulent flow is a fluid flow in which the velocity at a given point varies erratically in magnitude and direction. In some embodiments, the fluid flow through the constriction is laminar flow. Laminar flow involves uninterrupted flow in a fluid near a solid boundary in which the direction of flow at every point remains constant. In some embodiments, the fluid flow is turbulent flow after the cells pass through the constriction.

The velocity at which the cells pass through the constrictions can be varied. In some embodiments, the cells pass through the constrictions at a uniform cell speed. In some embodiments, the cells pass through the constrictions at a fluctuating cell speed.

IX. Exemplary Embodiments

A method for delivering a compound into a cell comprising a cell wall, the method comprising passing a cell suspension through a constriction, wherein said constriction deforms the cell comprising a cell wall, thereby causing a perturbation of the cell such that the compound enters the cell, wherein said cell suspension is contacted with the compound.

A method for delivering a compound into a cell modified to remove all or part of a cell wall, the method comprising passing a cell suspension through a constriction, wherein said constriction deforms the cell modified to remove all or part of a cell wall, thereby causing a perturbation of the cell such that the compound enters the cell, wherein said cell suspension is contacted with the compound.

A method for delivering a compound into a cell comprising a cell wall, the method comprising a) removing all or part of the cell wall, and b) passing the cell suspension through a constriction, wherein said constriction deforms the cell modified to remove all or part of a cell wall, thereby causing a perturbation of the cell such that the compound enters the cell, wherein said cell suspension is contacted with the compound.

The method of any one of embodiments 2-3, wherein all or part of the cell wall is removed prior to passing the cell suspension through the constriction by treating the cell suspension with an enzyme, heat or ultrasound.

The method of embodiment 4, wherein all or part of the cell wall is removed by treatment with an enzyme.

The method of embodiment 5, wherein the enzyme is one or more of cellulase, pectinase, xylanase, lysozyme, zymolyase, or chitinase.

The method of any one of embodiments 1-6, wherein the constriction is contained within a microfluidic channel.

The method of any one of embodiments 1-7, wherein the constriction is a pore or contained within a pore.

The method of embodiment 8, wherein the pore is contained in a surface.

The method of embodiment 9, wherein the surface is a filter.

The method of embodiment 9, wherein the surface is a membrane.

The method of any one of embodiments 1-11, wherein the constriction size is a function of the cell diameter.

The method of any one of embodiment 1-12, wherein the constriction size is about 20%, about 30%, about 40%, about 50%, about 60%, about 70%, about 80%, about 90%, or about 99% of the cell diameter.

The method of any one of embodiments 1-13, wherein the cell suspension comprises a mixed cell population.

The method of any one of embodiments 1-13, wherein the cell suspension comprises a purified cell population.

The method of any one of embodiments 1-15, wherein the cell comprising a cell wall or modified to remove all or part of a cell wall is a plant, yeast, fungal, algal, or prokaryotic cell.

The method of embodiment 16, wherein the plant cell is a crop, model, ornamental, vegetable, leguminous, conifer, or grass plant cell.

The method of embodiment 16, wherein the yeast cell is a *Candida, Hansenula, Kluyveromyces, Pichia, Saccharomyces, Schizosaccharomyces*, or *Yarrowia* strain cell.

The method of embodiment 16, wherein the fungal cell is an *Acremonium, Aspergillus, Fusarium, Humicola, Mucor, Myceliophthora, Neurospora, Penicillium, Scytalidium, Thielavia, Tolypocladium*, or *Trichoderma* strain cell.

The method of embodiment 16, wherein the prokaryotic cell is a *Bacillus coagulans, Bacteroides fragilis, Bacteroides melaninogenicus, Bacteroides oralis, Bifidobacterium bifidum, Bifidobacterium breve, Bifidobacterium infantis, Bifidobacterium lactis, Bifidobacterium longum, Carboxydocella* sp., *Clostridium perfringens, Clostridium septicum, Clostridium tetani, Corynebacterium glutamicum,* Enterobacteriaceae, *Enterococcus faecalis, Erwinia chrysanthemi, Faecalibacterium prausnitzii, Lactobacillus acidophilus, Lactobacillus brevis, Lactobacillus bulgaricus, Lactobacillus fermentum, Lactobacillus gasseri, Lactobacillus paracasei, Lactobacillus plantarum, Lactobacillus reuteri, Lactobacillus rhamnosus, Lactobacillus salivarius, Lactobacillus* sp., *Pediococcus acidilactici, Peptococcus* sp., *Peptostreptococcus* sp., *Propionibacterium freudenreichii, Proteus mirabilis, Pseudomonas aeruginosa, Rhodopseudomonas capsulata, Salmonella enteritidis, Staphylococcus aureus, Streptococcus faecium, Streptococcus lactis, Streptococcus salivarius, Streptococcus thermophilus, Vibrio furnissii, Caldicellulosiruptor saccharolyticus, Xanthomonas campestris,* cyanobacteria, *Escherichia, Enterobacter, Azotobacter, Erwinia, Bacillus, Pseudomonas, Klebsiella, Proteus, Salmonella, Serratia, Shigella, Rhizobia, Vitreoscilla, Synechococcus, Synechocystis*, or *Paracoccus* cell.

The method of embodiment 16, wherein the algal cell is a Chlorophyceae, Bacillariophyceae, Eustigmatophyceae, or Chrysophyceae cell.

The method of any one of embodiments 1-21, wherein the compound comprises a nucleic acid.

The method of any one of embodiments 1-22, wherein the compound comprises a nucleic acid encoding DNA, recombinant DNA, cDNA, genomic DNA, RNA, siRNA, mRNA, miRNA, lncRNA, tRNA, shRNA, or self-amplifying mRNA.

The method of any one of embodiments 1-23, wherein the compound comprises a transposon.

The method of any one of embodiments 1-24, wherein the compound is a plasmid.

The method of any one of embodiments 1-23, wherein the compound comprises a plastid.

The method of any one of embodiments 1-23, wherein the compound comprises a polypeptide-nucleic acid complex.

The method of any one of embodiments 1-23 or 27, wherein the compound comprises a Cas9 protein and a guide RNA or donor DNA.

The method of any one of embodiments 1-23, wherein the compound comprises nucleic acid encoding for a Cas9 protein and a guide RNA or donor DNA.

The method of any one of embodiments 1-23 or 27, wherein the compound comprises a transposase protein and a nucleic acid comprising a transposon.

The method of any one of embodiments 1-25, wherein the compound comprises a lipid-nucleic acid complex.

The method of any one of embodiments 1-25, wherein the compound comprises a cation-nucleic acid complex.

The method of any one of embodiments 1-21, wherein the compound comprises a polypeptide or peptide.

The method of any one of embodiments 1-22 or 33, wherein the compound comprises a TALEN protein, Zinc finger nuclease, mega nuclease, CRE recombinase, FLP recombinase, R recombinase, integrase, or transposase.

The method of any one of embodiments 1-21 or 33, wherein the compound comprises a histone acetyltransferase, deacetylase, methyltransferase, or demethylase.

The method of any one of embodiments 1-21 or 33, wherein the compound is an antibody.

The method of any one of embodiments 1-21 or 33, wherein the compound is a transcription factor.

The method of any one of embodiments 1-21, wherein the compound is a small molecule.

The method of any one of embodiments 1-21, wherein the compound is a nanoparticle.

The method of any one of embodiments 1-21, wherein the compound is a liposome.

The method of any one of embodiments 1-21, wherein the compound is a fluorescently tagged molecule.

EXAMPLES

Example 1: Delivery to *S. cerevisiae* Cells

In order to evaluate the constriction-mediated delivery of molecules into cells comprising cell walls, *S. cerevisiae* cells mixed with fluorescent dextran particles are passed through a constriction, and intracellular particle delivery is evaluated. The cells are pre-incubated with chemicals to remove the cell wall prior to passing through the constriction. Alternatively, the cells are not incubated with chemicals and the cell wall is intact prior to passing through the constriction. The cells are passed through a constriction within a microfluidic channel, or through a surface containing pores. Pressure, temperature, and buffer composition are optimized to achieve delivery. Fluorescence detection is used to measure the delivery efficiency of the dextran particles into the cells.

In vitro studies were carried out to evaluate the constriction-mediated delivery of molecules into *S. cerevisiae*. *S. cerevisiae* cells were grown overnight in yeast extract-peptone-dextrose (YPD) medium. Cells were treated with 0.3 U zymolyase for nine minutes at room temperature to partially digest cell walls without significant cell lysis. Treated cells were collected by centrifugation and resuspended at $1\times10^8$ cells/mL in PBS at room temperature. The resuspended cells were mixed with 10 μg/mL plasmid DNA for expressing the nourseothricin N-acetyl transferase (NAT) gene, which confers resistance to nourseothricin (NTC), and 11 μM of free Alexa Fluor® 488, and passed through a track etched polycarbonate surface containing 3 μm pores. Additionally, cells mixed with either plasmid DNA alone or plasmid DNA+free Alexa Fluor® 488, without constriction, were included as endocytosis controls. The cells were then characterized by flow cytometry where dead cells were stained with propidium iodide and excluded from analysis. As shown in FIG. 1 (top row of dot-plots), passage through the pores resulted in fewer live cells compared to the endocytosis controls, as can be expected upon perturbation of the cell membrane. Live cells were then assessed for incorporation of Alexa Fluor® 488 by flow cytometry. Endocytosis accounted for only a small portion of Alexa Fluor® 488-positive cells following constriction, as indicated by the difference in peak shift between the DNA+Alexa Fluor® 488 endocytosis control condition and the constriction conditions shown in FIG. 1 (bottom row of histograms).

Figure 2:
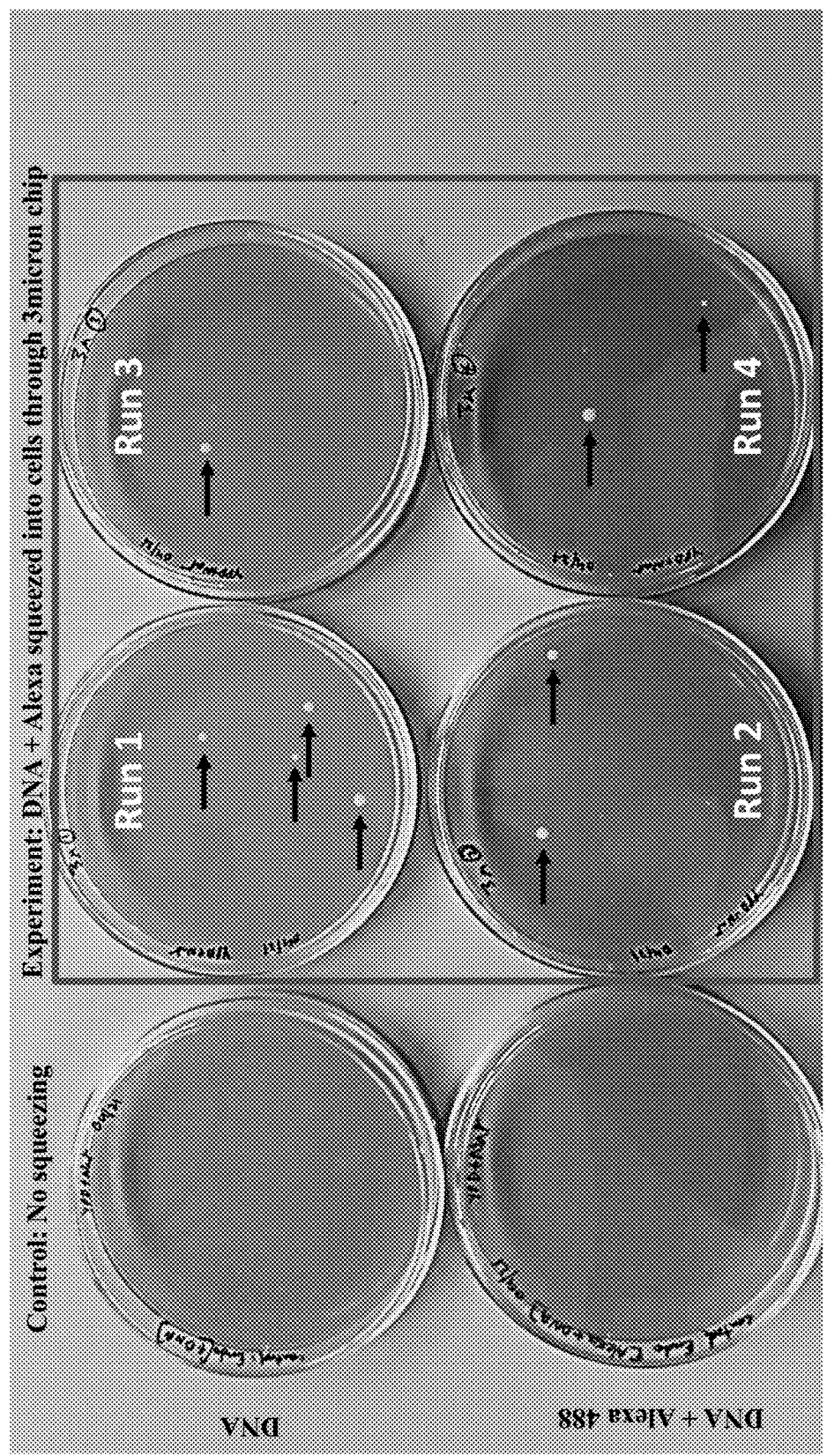
FIG. 2 shows the results of selection on YPD+NTC plates for S. cerevisiae cells following constriction-mediated delivery of a plasmid conferring NTC resistance. NTC-resistant colonies indicated by arrows.

Live cells were spread on YPD agar plates containing NTC and incubated for 3 days to allow for growth of *S. cerevisiae* cells that had successful delivery of the plasmid DNA and expression of the NTC resistance gene. As shown in FIG. 2, NTC-resistant colonies were present on plates spread with cells mixed with the plasmid DNA and passed through the pores, but not on the plates spread with cells mixed with plasmid DNA without constriction. Individual colonies were re-streaked on selection plates containing NTC, confirming delivery and expression of the plasmid DNA. These results demonstrate that the constriction-mediated delivery approaches described herein are practical for use in cells having a cell wall.

What is claimed is:

1. A method for delivering a compound into a modified cell which has been modified to remove all or part of a cell wall, the method comprising passing a cell suspension which comprises the modified cell through a constriction, wherein the constriction deforms the modified cell, thereby causing a perturbation of the modified cell such that the compound enters the modified cell through the perturbation when contacted with the modified cell, and wherein the constriction is a pore or contained within a pore.

2. The method of claim 1, wherein the pore is contained in a surface.

3. The method of claim 2, wherein the surface is a filter or a membrane.

4. The method of claim 1, wherein the constriction comprises a size which is about 20% to about 99% of a diameter of the modified cell.

5. The method of claim 4, wherein the size of the constriction is about 20%, about 30%, about 40%, about 50%, about 60%, about 70%, about 80%, about 90%, or 99% of the diameter of the modified cell.

6. The method of claim 1, wherein the cell suspension comprises a mixed cell population or a purified cell population.

7. The method of claim 1, wherein the modified cell is a plant cell, yeast cell, fungal cell, algal cell, or prokaryotic cell.

8. The method of claim 7, wherein:
(a) the plant cell is a crop, model, ornamental, vegetable, leguminous, conifer, or grass plant cell;
(b) the yeast cell is a *Candida, Hansenula, Kluyveromyces, Pichia, Saccharomyces, Schizosaccharomyces*, or *Yarrowia* strain cell;
(c) the fungal cell is an *Acremonium, Aspergillus, Fusarium, Humicola, Mucor, Myceliophthora, Neurospora, Penicillium, Scytalidium, Thielavia, Tolypocladium*, or *Trichoderma* strain cell;
(d) the prokaryotic cell is a *Bacillus coagulans, Bacteroides fragilis, Bacteroides melaninogenicus, Bacteroides oralis, Bifidobacterium bifidum, Bifidobacterium breve, Bifidobacterium infantis, Bifidobacterium lactis, Bifidobacterium longum, Carboxydocella* sp., *Clostridium perfringens, Clostridium septicum, Clostridium tetani, Corynebacterium glutamicum, Enterobacteriaceae, Enterococcus faecalis, Erwinia chrysanthemi, Faecalibacterium prausnitzii, Lactobacillus acidophilus, Lactobacillus brevis, Lactobacillus bulgaricus, Lactobacillus fermentum, Lactobacillus gasseri, Lactobacillus paracasei, Lactobacillus plantarum, Lactobacillus reuteri, Lactobacillus rhamnosus, Lactobacillus salivarius, Lactobacillus* sp., *Pediococcus acidilactici, Peptococcus* sp., *Peptostreptococcus* sp., *Propionibacterium freudenreichii, Proteus mirabilis, Pseudomonas aeruginosa, Rhodopseudomonas capsulata, Salmonella enteritidis, Staphylococcus aureus, Streptococcus faecium, Streptococcus lactis, Streptococcus salivarius, Streptococcus thermophilus, Vibrio furnissii, Caldicellulosiruptor saccharolyticus, Xanthomonas campestris*, cyanobacteria, *Escherichia, Enterobacter, Azotobacter, Erwinia, Bacillus, Pseudomonas, Klebsiella, Proteus, Salmonella, Serratia, Shigella, Rhizobia, Vitreoscilla, Synechococcus, Synechocystis*, or *Paracoccus* cell; or
(e) the algal cell is a Chlorophyceae, Bacillariophyceae, Eustigmatophyceae, or Chrysophyceae cell.

9. The method of claim 1, wherein the compound comprises a nucleic acid or a polypeptide-nucleic acid complex.

10. The method of claim 9, wherein the nucleic acid comprises a DNA, recombinant DNA, cDNA, genomic DNA, RNA, siRNA, mRNA, mRNA, lncRNA, tRNA, shRNA, or self-amplifying mRNA.

11. The method of claim 1, wherein the compound comprises a transposon, a plastid, a lipid-nucleic acid complex, a cation-nucleic acid complex, a polypeptide or peptide, a small molecule, a nanoparticle, a fluorescently tagged molecule, or a liposome.

12. The method of claim 1, wherein the compound is a plasmid.

13. The method of claim 1, wherein: (a) the compound comprises a Cas9 protein and a guide RNA or donor DNA; or (b) the compound comprises nucleic acid encoding for a Cas9 protein and a guide RNA or donor DNA; or (c) the compound comprises a transposase protein and a nucleic acid comprising a transposon.

14. The method of claim 1, wherein:
(a) the compound comprises a TALEN protein, Zinc finger nuclease, mega nuclease, CRE recombinase, FLP recombinase, R recombinase, integrase, or transposase; or
(b) the compound comprises a histone acetyltransferase, deacetylase, methyltransferase, or demethylase; or
(c) the compound comprises an antibody; or
(d) the compound is a transcription factor.

15. A method for delivering a compound into a cell comprising a cell wall, the method comprising a) removing all or part of the cell wall to produce a modified cell, and b) passing a cell suspension comprising the modified cell through a constriction, wherein the constriction deforms the modified cell, thereby causing a perturbation of the modified cell such that the compound enters the modified cell through the perturbation when contacted with the modified cell, and wherein the constriction is a pore or contained within a pore.

16. The method of claim 15, wherein removing all or part of the cell wall comprises treating the cell with an enzyme, heat, or ultrasound.

17. The method of claim 16, wherein the enzyme is one or more of cellulase, pectinase, xylanase, lysozyme, an enzyme preparation comprising β-1,3-glucan laminaripentaohydrolase and β-1,3-glucanase, or chitinase.

18. The method of claim 15, wherein the pore is contained in a surface.

19. The method of claim 18, wherein the surface is a filter or a membrane.

20. The method of claim 15, wherein the cell comprises a plant cell, yeast cell, fungal cell, algal cell, or prokaryotic cell.

21. The method of claim 15, wherein the compound comprises a nucleic acid or a polypeptide-nucleic acid complex.

22. The method of claim 15, wherein the compound comprises a transposon, a plastid, a lipid-nucleic acid complex, a cation-nucleic acid complex, a polypeptide or peptide, a small molecule, a nanoparticle, a fluorescently tagged molecule, or a liposome.

23. The method of claim 15, wherein the compound is a plasmid.

24. The method of claim 15, wherein: (a) the compound comprises a Cas9 protein and a guide RNA or donor DNA; or (b) the compound comprises nucleic acid encoding for a Cas9 protein and a guide RNA or donor DNA; or (c) the compound comprises a transposase protein and a nucleic acid comprising a transposon.

25. The method of claim 15, wherein:
(a) the compound comprises a TALEN protein, Zinc finger nuclease, mega nuclease, CRE recombinase, FLP recombinase, R recombinase, integrase, or transposase; or
(b) the compound comprises a histone acetyltransferase, deacetylase, methyltransferase, or demethylase; or
(c) the compound comprises an antibody; or
(d) the compound is a transcription factor.

* * * * *